United States Patent
Alford et al.

(10) Patent No.: US 12,187,784 B2
(45) Date of Patent: Jan. 7, 2025

(54) PROCESSES FOR MAKING A CELLULAR FIBRONECTIN COMPOSITION

(71) Applicant: COMBANGIO, INC., Menlo Park, CA (US)

(72) Inventors: Spencer Alford, Newark, CA (US); Audrey Smith, Menlo Park, CA (US)

(73) Assignee: COMBANGIO, INC., Menlo Park, CA (US)

( * ) Notice: Subject to any disclaimer, the term of this patent is extended or adjusted under 35 U.S.C. 154(b) by 0 days.

(21) Appl. No.: 17/856,944

(22) Filed: Jul. 1, 2022

(65) Prior Publication Data

US 2023/0000954 A1  Jan. 5, 2023

Related U.S. Application Data

(60) Provisional application No. 63/235,605, filed on Aug. 20, 2021, provisional application No. 63/217,952, filed on Jul. 2, 2021.

(51) Int. Cl.

| | | |
|---|---|---|
| *C07K 14/78* | (2006.01) |
| *A61K 9/16* | (2006.01) |
| *A61K 35/28* | (2015.01) |
| *A61K 38/17* | (2006.01) |
| *A61K 38/18* | (2006.01) |
| *A61K 38/36* | (2006.01) |
| *A61K 38/39* | (2006.01) |
| *A61K 45/06* | (2006.01) |

(Continued)

(52) U.S. Cl.
CPC ............ *C07K 14/78* (2013.01); *A61K 9/1623* (2013.01); *A61K 35/28* (2013.01); *A61K 38/1709* (2013.01); *A61K 38/177* (2013.01); *A61K 38/1833* (2013.01); *A61K 38/1858* (2013.01); *A61K 38/1866* (2013.01); *A61K 38/36* (2013.01); *A61K 38/39* (2013.01); *A61K 45/06* (2013.01); *A61K 47/02* (2013.01); *A61K 47/26* (2013.01); *A61P 27/02* (2018.01); *C07K 14/475* (2013.01); *C12N 5/0663* (2013.01); *C12N 5/0668* (2013.01)

(58) Field of Classification Search
None
See application file for complete search history.

(56) References Cited

U.S. PATENT DOCUMENTS

| | | | |
|---|---|---|---|
| 4,728,637 A | 3/1988 | Silverman |
| 5,053,334 A | 10/1991 | Arathoon et al. |
| | (Continued) | | |

FOREIGN PATENT DOCUMENTS

| | | | |
|---|---|---|---|
| WO | WO 2012/079086 A1 * | 6/2012 |
| WO | WO 2016/17858 | 11/2016 |
| WO | WO 2019/016799 | 1/2019 |

OTHER PUBLICATIONS

Lembong et al. (2020, Bioengineering 7(73):pp. 1-16; doi:10.3390/bioengineering7030073).*

(Continued)

*Primary Examiner* — Elizabeth C. Kemmerer
(74) *Attorney, Agent, or Firm* — Morgan, Lewis & Bockius LLP; Christina A. MacDougall

(57) ABSTRACT

The present application provides methods and processes for making and using a fibronectin composition, as well as methods for treating ocular conditions and/or disorders with the cellular fibronectin composition described herein.

20 Claims, 7 Drawing Sheets

(51) Int. Cl.
  *A61K 47/02* (2006.01)
  *A61K 47/26* (2006.01)
  *A61P 27/02* (2006.01)
  *C07K 14/475* (2006.01)
  *C12N 5/0775* (2010.01)

(56) References Cited

U.S. PATENT DOCUMENTS

| | | | |
|---|---|---|---|
| 5,750,378 A * | 5/1998 | Goodheart | C07K 14/78 435/405 |
| 6,372,494 B1 | 4/2002 | Naughton et al. | |
| 2011/0021750 A1* | 1/2011 | Yu | G01N 33/57484 530/350 |
| 2011/0177593 A1 | 7/2011 | Funaki et al. | |

OTHER PUBLICATIONS

"Medium 199", https://www.sigmaaldrich.com/US/en/products/cell-culture-and-analysis/cell-culture-media-and-buffers/classical-media-and-buffers/medium-199; accessed Feb. 29, 2024.*
Najar et al. (2016, Cytotherapy 18:320-335).*
Juhl et al. (2016, Scandinavian Journal of Clinical & Laboratory Investigation 76(2):93-104).*
Zeng et al. (2016, J Biomed Mater Res Part A 104A:1902-1911).*
Branscome et al. (2020, J. Neuroimmune Pharmacology 15:520-537).*
Kosol et al. (2020, Biochemical and Biophysical Research Communications 522:335-341).*
PCT International Search Report dated Oct. 11, 2022, for corresponding PCT/US2022/036036, 1 page.
Zeng et al., 'Bone Marrow Mesenchymal Stem Cells in a Three-Dimensional Gelatin Sponge Scaffold Attenuate Inflammation, Promote Angiogenesis, and Reduce Cavity Formation in Experimental Spinal Cord Injury. Cell Transplantation', vol. 20, pp. 1881-1899, 2011.
Zeng et al., 'Autocrine fibronectin from differentiating mesenchymal stem cells induces the neurite elongation in vitro and promotes nerve fiber regeneration in transected spinal cord injury'. Journal of Biomedical Materials Research A, Aug. 2016 vol. 104A, Issue 8, p. 1902-1911.

Atherton et al. Cell 25:133-41 (1981).
Batzer et al., Nucleic Acid Res. 19:5081, (1991).
Bourin et al., Cytotherapy, 15(6):641-648 (2013).
Brighton, et al., The Journal of Bone and Joint Surgery 73(6):832-47 (1991).
Dietrich-Ntoukas et al. Cornea., 31(3):299-310 (2012).
Gaudana et al. Pharm Res. 26(5):1197-216 (2009).
Hayashi et al. J. Biol. Chem. 256(21):11,292-11,300 (1981).
Kaltz, et al., Exp Cell Res Oct. 1;316(16):2609-17 (2010).
Kornblihtt et al., Nucleic Acids Res. 12(14):5853-68 (1984).
Kornblihtt et al., EMBO J. 3(1):221-26 (1984).
Kornblihtt et al. EMBO J. 4(7):1755-59 (1985).
Liang et al., Nat Protoc 2, 329-333 (2007).
McCulley, JP et al. Trans Am Ophthalmol Soc.; 91:367-86 (1993).
Ohtsuka et al., Biol. Chem. 260:2605-2608, (1985).
Rahman et al., BMC cell biology 6(1):8 (2005).
Rossolini et al., Mol. Cell. Probes 8:91-98 (1994).
Sani et al., Science Advances, vol. 5, No. 3 (2019).
Schwarzbauer et al., Proc. Natl. Acad. Sci. USA., 82:1424-28 (1985).
Stevenson, et al., Clin Ophthalmol. 7:2153-2158 (2013).
Tamkun et al., J. Biol. Chem. 258(7):4641-47 (1983).
To, W.S. et al., Fibrogenesis Tissue Repair 4, 21 (2011).
Turner, et al., J Neurosurg 118(5):1072-1085 (2013).
Van Stavern, et al., J Neuro-Ophthalmol 21(2):112-117 (2001).
White et al. The Journal of Pathology. vol. 216(1): 1-14 (2008).
White and Muro, IUBMB Life, 63: 538-546 (2011).
White et al., J Allergy Clin Immunol Pract. 6(1):38-69 (2018).
Wirostko B, et al., Ocul Surf. Jul; 13(3): 204-21 (2015).
Yamada et al., J. Cell Biol. 80:492-98 (1979).
Yamada et al. Biochemistry 16(25):5552-9 (1977).
Neuss et al. (2004, Stem Cells 22:405-414).
Deans and Moseley (2000, Experimental Hematology, 875-884).
Manuguerra-Gagné et al., Stem Cells, 2013;31:1136-1148.
Oh et al., Stem Cells, 2008;26:1047-1055.
Phan et al., 1991; 109:414-419.
Quest Calculate™ PBS (Phosphate Buffered Saline) (1X, pH 7.4) Preparation and Recipe. AAT Bioquest, Inc., Sep. 26, 2023, https://www.aatbio.com/resources/buffer-preparations-and-recipes/pbs-phosphate-buffered-saline.

* cited by examiner

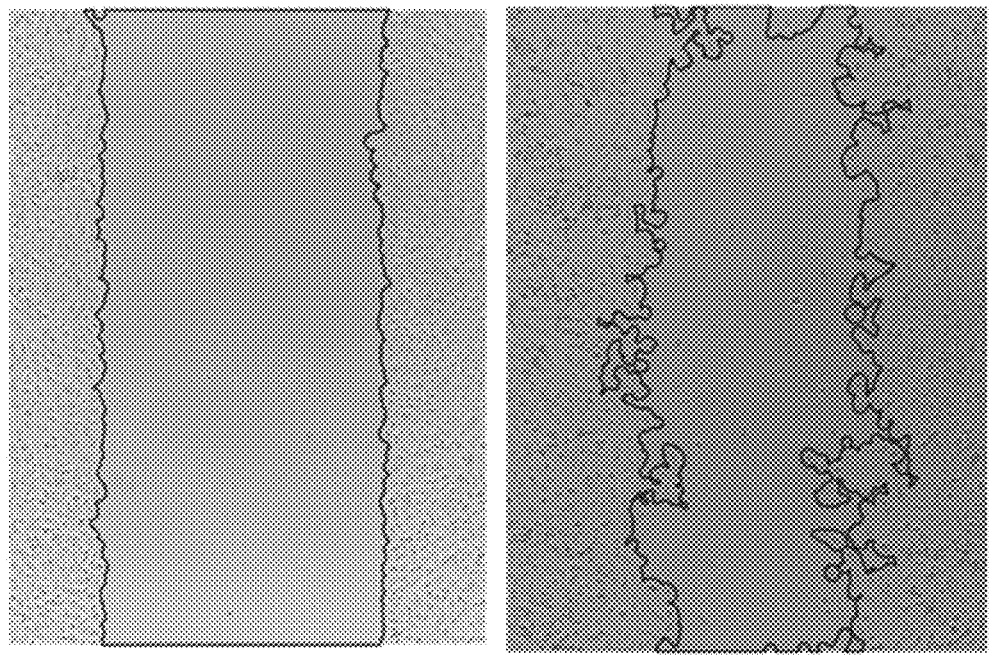
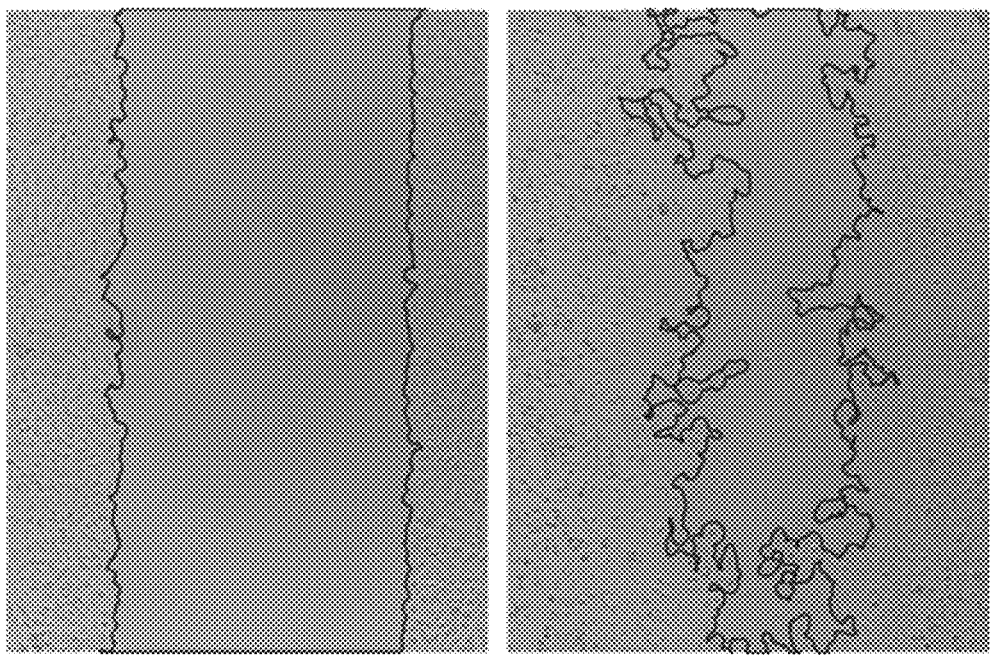
Fig. 4

Fig. 5

| HGF Concentration (pg/mL) ||
|---|---|
| In-solution fraction | Bead fraction |
| 39 | 54262 |

PROCESSES FOR MAKING A CELLULAR FIBRONECTIN COMPOSITION

CROSS-REFERENCE TO RELATED APPLICATIONS

This application claims priority to U.S. Provisional Application No. 63/217,952, filed Jul. 2, 2021, and U.S. Provisional Application No. 63/235,605, filed Aug. 20, 2021, all of which are herein incorporated by reference in their entireties.

BACKGROUND OF THE INVENTION

Blast and blunt injuries to the eye can cause a series of mechanical disruptions to the ocular contents including commotio retinae, traumatic cataract, disruption of the zonular attachments to the lens, angle recession, iris dialysis, and rupture of the pupillary sphincter. Treatment of these injuries has been limited to mechanical repair (when possible) of the iris, replacement of the crystalline lens with plastic lens implants, and repair of retinal detachments. There has been no treatment to repair the cellular architecture of the retina or the anterior chamber. Furthermore, traumatic optic neuropathy and optic nerve avulsion are among the six leading types of ocular injury that required specialized ophthalmic care during Operation Iraqi Freedom (Cho and Savitsky, "Ocular Trauma Chapter 7", in Combat Casualty Care: Lessons learned from Oef and Oif, by Brian Eastbridge and Eric Savitsky, pp. 299-342, Ft. Detrick, Md.: Borden Institute (US) Government Printing Office, 2012), incorporated herein by reference in its entirety. Sixty percent of traumatic head injuries result in neuro-ophthalmic abnormalities (Van Stavern, et al., *J Neuro-Ophthamol* 21(2):112-117, 2001) (incorporated herein by reference in its entirety) half of which involve the optic nerves or visual pathways. Traumatic injury to neurons results in axonal damage and irreversible neuronal loss resulting in permanent deficits. While a number of potential neuroprotective therapies have been identified in animals, these single agents have generally failed to translate to therapies in human clinical trials (Turner, et al., *J Neurosurg* 118(5):1072-1085, 2013, incorporated herein by reference in its entirety). Combination therapies that affect several cellular targets are likely needed to prevent neuronal damage.

The cornea serves a protective role as the outermost tissue of the eye; however it is highly vulnerable to severe injury and disease. Its lack of blood vessels enables its transparency but also limits its ability to heal. Corneal injury, due to its potential to cause irreversible blindness, requires prompt intervention and aggressive treatment. The critical need for improved ocular surface healing therapies is particularly apparent for chemical burns and in severe corneal diseases, such as ocular manifestations of acute Chronic Graft v. Host Disease (GvHD), Stevens-Johnson Syndrome, Ocular Mucous Membrane Pemphigoid and other conditions giving rise to persistent corneal epithelial defect, which collectively comprise an incidence of over 100,000 cases per year. (See, Dietrich-Ntoukas et al. Cornea. 2012, 31(3):299-310; Stevenson W, et al., *Clin Ophthalmol.* 2013, 7:2153-2158. White K D, et al., *J Allergy Clin Immunol Pract.* 2018; 6(1):38-69; Tauber J. (2002) Autoimmune Diseases Affecting the Ocular Surface. In: Ocular Surface Disease Medical and Surgical Management. Springer, New York, NY; and Wirostko B, et al., *Ocul Surf* 2015 July; 13(3): 204-21; and Haring, R S., et al., *JAMA Ophthalmol.* 2016 Oct. 1; 134(10):1119-1124.)

Moreover, topical ophthalmic drug development is impeded by many anatomical constraints including tear turnover and dilution, nasolacrimal drainage, and reflex blinking with often less than 5% of the topically administered dose reaching deeper ocular tissues (Gaudana et al., 2009). In the case of corneal wounds, the initial insult causes rifts in the corneal epithelium thereby enabling the passage of topically applied MSC-S to penetrate the epithelial layers.

Accordingly, there is a large unmet need in the art for ocular therapies that can target the eye and deliver a therapeutic payload to difficult-to-reach sensory tissue which may have degenerated due to inflammation secondary to trauma (such as for example, burns, acute inflammation, age, and/or oxidative stress).

BRIEF SUMMARY OF THE INVENTION

The present invention meets this need by providing compositions comprising fibronectin, optionally one or more growth factors that are non-covalently attached to the fibronectin (FN), for use in such treatments, as well as methods for making such compositions.

In some embodiments, the FN is MSC-derived FN.

In some embodiments, the FN is MSC-secreted FN.

In some embodiments, the FN is cellular FN.

In some embodiments, the cellular FN is cellularly derived FN, and wherein the FN is non-covalently attached to one or more growth factors.

In some embodiments, the cellular FN is EDA+ and/or EDB+.

In some embodiments, the cellular fibronectin is obtained from a conditioned medium.

In some embodiments, the cellular fibronectin is secreted by mesenchymal stem cells (MSCs).

In some embodiments, the conditioned medium is obtained from a culture of MSCs.

In some embodiments, the composition comprises an MSC secretome.

In some embodiments, the MSCs are derived from bone marrow. In some embodiments, the MSCs are derived from the bone marrow from a healthy human donor.

In some embodiments, the composition further comprises one or more growth factors selected from the group consisting of FGFs (such as FGF-2), PDGF, HGF, VEGF, TGFβ1, TGFβ2, IGF-1, IGF-2, NGF, neurotrophins, and EGF.

In some embodiments, the cellular fibronectin is bound to one or more growth factors selected from the group consisting of FGFs (such as FGF-2), PDGF, HGF, VEGF, TGFβ1, TGFβ2, IGF-1, IGF-2, NGF, neurotrophins, and EGF.

In some embodiments, the cellular fibronectin in the composition is at a concentration of about 0.5-50 ng/mL.

In some embodiments, the cellular fibronectin in the composition is at a concentration of about 25 ng/mL.

In some embodiments, the composition further comprises at least about 0.1 ng/mL PDGF.

In some embodiments, the composition further comprises about 0.3-4.5 ng/mL HGF.

In some embodiments, the composition further comprises about 1 pg/mL-400 pg/mL of VEGF.

In some embodiments, the composition further comprises a tonicity modifying agent. In some embodiments, the tonicity modifying agent is selected from the group consisting of NaCl, KCl, mannitol, dextrose, sucrose, sorbitol, and glycerin.

In some embodiments, the composition comprises: 0.5-50 ng/mL FN, 2.28 mg/mL monobasic sodium phosphate, 10-12 mg/mL dibasic sodium phosphate, 11-13 mg/mL mannitol, 2-25 mg/mL trehalose dihydrate, and 0.5-2 mg/mL Hypromellose.

In some embodiments, the composition comprises: 0.5-50 ng/mL FN, 2.28 mg/mL monobasic sodium phosphate, 11.45 mg/mL dibasic sodium phosphate, 12.2 mg/mL mannitol, 24 mg/mL trehalose dihydrate, and 1 mg/mL Hypromellose.

In some embodiments, the composition comprises: 0.5-50 ng/mL FN, 1.31 mg/mL monobasic sodium phosphate, 4.5-7 mg/mL dibasic sodium phosphate, 5.5-7.5 mg/mL mannitol, 11-13 mg/mL trehalose dihydrate, and 0.1-1.5 mg/mL Hypromellose. In some embodiments, the FN composition does not comprise NaCl and/or $MgCl_2$.

In some embodiments, the composition comprises: 0.5-50 ng/mL FN, 1.31 mg/mL monobasic sodium phosphate, 5.73 mg/mL dibasic sodium phosphate, 6.1 mg/mL mannitol, 12 mg/mL trehalose dihydrate, and 0.5 mg/mL Hypromellose.

In some embodiments, the composition does not comprise NaCl and/or $MgCl_2$.

In some embodiments, the present disclosures herein provide a method of treatment for an ocular condition in a subject in need thereof comprising administering to the subject the composition provided herein.

In some embodiments, the ocular condition is selected from the group consisting of retina condition, Chronic Graft v. Host Disease (GvHD), Stevens-Johnson Syndrome, Ocular Mucous Membrane Pemphigoid, Persistent Corneal Epithelial Defect (PCED), dry eye, ocular nerve tissue damage, and concussive injury to the eye (such as concussive injury, ocular contusion, or chemical burn).

In some embodiments, the present disclosures herein provide the use of the composition for treating an ocular condition in a subject in need thereof according to the method disclosed herein.

In some embodiments, the present disclosures herein provide a method of making an FN composition, comprising:
(a) culturing stem cells in a cell culture medium, thereby generating conditioned medium that comprises factors secreted by the stem;
(b) harvesting the conditioned medium thereby producing harvested conditioned medium; and
(c) filtering harvested conditioned medium to produce processed conditioned medium.

In some embodiments, the method further comprises concentrating the processed conditioned medium.

In some embodiments, the processed conditioned medium further undergoes buffer exchange with a formulation buffer.

In some embodiments, the formulation buffer comprises one or more of di/mono sodium phosphate, sodium citrate/citric acid, boric acid/sodium citrate, boric acid/sodium tetraborate, and citric acid/disodium phosphate.

In some embodiments, the stem cells are mesenchymal stem cells (MSCs).

In some embodiments, the cell culture medium is serum free.

In some embodiments, the method of producing prior to step (a) further comprises:
(i) culturing the stem cells in a growth medium; and
(ii) replacing the growth medium with the cell culture medium of step (a).

BRIEF DESCRIPTION OF THE DRAWINGS

FIG. 4. Depletion of Fibronectin impairs human corneal epithelial cell in vitro wound closure.

FIG. 5. Provides data showing immunoprecipitated fibronectin contains bound HGF.

DETAILED DESCRIPTION OF THE INVENTION

I. Introduction

Figure 1:
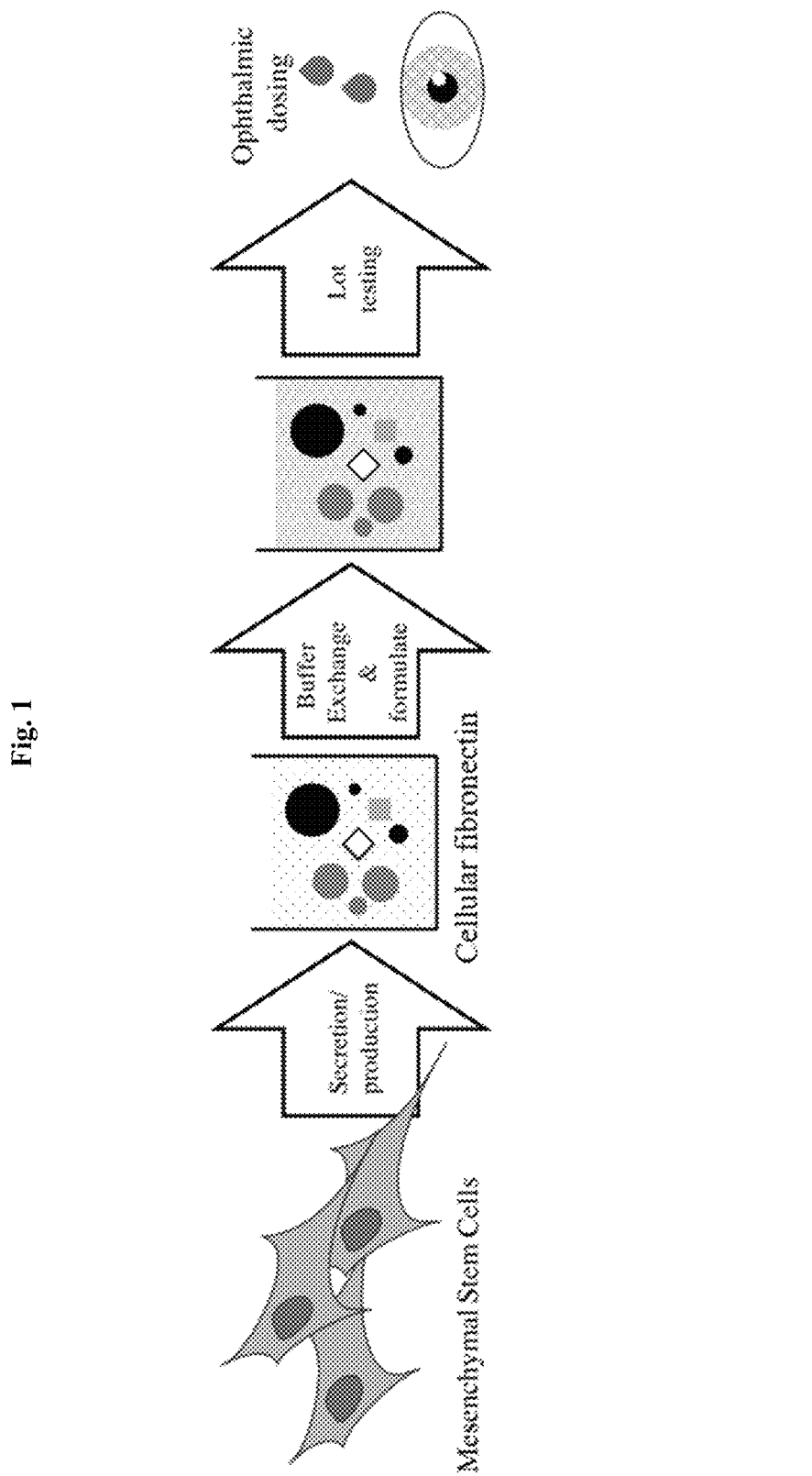
FIG. 1. Schematic diagram of an embodiment of fibronectin preparation, processing, and use.

Fibronectin (FN) is a large glycoprotein containing around 5% carbohydrate. The characteristic form of plasma fibronectin is a disulfide-bonded dimer of 440,000 daltons, each subunit having a molecular weight of about 220,000 daltons. Normally found in plasma at a concentration of about 300 μg/mL, fibronectin is extracted and purified using a method described by Hynes, R. O., Methods for identification of fibronectin (chap. 2, page 12), IN: Fibronectins New-York: Springer-Verlag, 1990. Plasma fibronectin is also known by various other names, including cold-insoluble globulin, anti-gelatin factor, cell attachment protein, cell spreading factor, and opsonic α2-surface binding glycoprotein. These names reflect biological activities of fibronectin such as cell recruitment, opsonization of particulate debris, and promotion of wound contraction. Descriptions of structure and activities of fibronectin can be found in Hynes, R. O., Methods for identification of fibronectin (chap. 2, page 12), IN: Fibronectins New-York: Springer-Verlag, 1990, and Hynes, R. O., Methods for identification of fibronectin (chap. 2, pages 7-23) and Wound healing, inflammation, and fibrosis (chap. 14, pages 349-64), IN: Fibronectins New-York: Springer-Verlag, 1990. 3, and Brotchie, H., Wakefield, D. *Australas J Dermatol* 1990; 31:47-56 (all incorporated herein by reference in their entireties).

Wound healing is usually divided into three phases: the inflammatory phase, the proliferative phase, and the remodeling phase. Fibronectin has been reported to be involved in each stage of the wound healing process, particularly by creating a scaffold to which the invading cells can adhere. Initially, many mediators, such as fibronectin and fibrinogen, are released to the wound site. Fibronectin promotes inflammatory cells migration into the wound and debris phagocytosis by the monocytes. Thereafter, angiogenesis and re-epithelialization take place. At this stage fibronectin exerts chemotactic activity on endothelial cells and promotes the migration of epithelial cells and fibroblasts onto the basal membrane.

Fibronectin also appears to be an essential component of the remodeling phase where it plays a major role in the organization of collagen fibrils. The fibrillar collagen ultimately forms fibrous bundles that greatly enhance the tissue tensile strength, leading to wound closure. Plasma fibronectin has been reported as being useful for increasing the rate of wound healing such as in corneal wounds and leg ulcers.

There are two forms of fibronectin: plasma fibronectin and cellular fibronectin. Plasma fibronectin is synthesized and secreted by hepatocytes into the blood plasma, while cellular fibronectin is produced by many cell types such as fibroblasts, endothelial cells, stem cells, myocytes and chondrocytes.

In wound healing, it has been reported that plasma fibronectin accumulates remarkably in the wound after wounding in vivo, which is crucial for various functions of platelets, fibroblasts and endothelial cells such as adhesion, migration and aggregation, revealing that plasma fibronectin is likely to serve as a suitable substrate to accelerate wound repair in vivo. Indeed, in animal model, provisional matrix containing plasma fibronectin significantly supports epidermal cell adhesion and migration in the re-epithelialization process, showing the clinical potential of plasma fibronectin in human wound healing and tissue repair.

Despite extensive physical and immunologic similarities, the two classes of fibronectin differ in electrophoretic behavior, solubility, and biologic activities. Tamkun et al., *J. Biol. Chem.* 258(7):4641-47 (1983); Yamada et al., *J. Cell Biol.* 80:492-98 (1979); Yamada et al. Biochemistry 16(25):2552-59 (1977).

Moreover, primary structural differences between plasma and cellular fibronectins have been found by peptide mapping, Hayashi et al. *J. Biol. Chem.* 256(21):11,292-11,300 (1981), and immunologic techniques, Atherton et al. *Cell* 25:133-41 (1981). Recently, a difference region encoding for exactly one 90 amino acid type III structural repeat was identified in mRNA from human fibroblasts and two human tumor cell lines, but could not be detected in human liver mRNA. Kornblihtt et al. *EMBO J.* 4(7):1755-59 (1985); Kornblihtt et al., *EMBO J.* 3(1):221-26 (1984); Kornblihtt et al., *Nucleic Acids Res.* 12(14):5853-68 (1984). Since plasma fibronectin is synthesized by hepatocytes, it is likely that the extra type III repeat is a unique domain of cellular fibronectins. Schwarzbauer et al., *Proc. Natl. Acad. Sci. USA.,* 82:1424-28 (1985); Kornblihtt et al., *EMBO J.* 3(1):221-26 (1984); Kornblihtt et al., *Nucleic Acids Res.* 12(14):5853-68 (1984). Additional discussion of the differences between plasma fibronectin and cellular fibronectin are provided in W. S., et al., *Fibrogenesis Tissue Repair* 4, 21 (2011).

Cellular fibronectin is characterized by fibronectin splice variants that are absent in the circulating plasma fibronectin pool. These alternative splice variants render Fibronectin sequences harboring extra domains (type III domains), called EIIIA and EIIIB (or EDA and EDB). White et al. *The Journal of pathology.* vol. 216(1): 1-14 (2008); White and Muro, *IUBMB Life,* 63: 538-546 (2011). Therefore, in some embodiments, cellular fibronectin is EDA+ and/or EDB+. In some embodiments, cellular fibronectin is EDA+, EDB+, and/or V+. In some embodiments, cellular fibronectin is EDA+. In some embodiments, cellular fibronectin is EDB+. In some embodiments, cellular fibronectin is V+. One or both type III domains may be incorporated. Cellular fibronectin may be a mixture of these isoforms.

Despite the tremendous interest in the therapeutic application of fibronectin in promoting wound healing, clinical studies to date have been focused on plasma fibronectin. No clinical study on cellular fibronectin has so far been reported and clinical studies on plasma fibronectin showed inconsistent results among patients with ocular diseases. For example, McCulley, J P. et al. reported that patients with persistent corneal epithelial defects disappointingly failed to respond to plasma fibronectin treatment. McCulley J P, Horowitz B, Husseini Z M, Horowitz M. *Trans Am Ophthalmol Soc.* 1993; 91:367-86; discussion 386-90.

A growing body of studies show that growth factors can bind to FN at various sites. As such, FN may act as an effective reservoir retaining growth factors to increase their local concentrations in physiological microenvironment. For example, it was reported that HGF binds the HGF receptor and integrins as well as FN to assemble into multimeric complexes in promoting cell migration. Rahman, Salman et al., *BMC cell biology* vol. 6, 1 8. 17 Feb. 2005. FN was also found to bind via its C-terminal heparin-II domain (FN III) to various growth factors in the PDGFNEGF and FGF families, and some growth factors from the transforming growth factor-β (TGF-β) and neurotrophin families. Although FN-sequestered growth factors supposedly possess localized, prolonged and enhanced GF activity, development of recombinant combination therapy with recombinant FN and growth factors that retain their endogenous biochemical and biophysical attributes remains challenging.

A. Definitions

Terms used in the claims and specification are defined as set forth below unless otherwise specified. In the case of direct conflict with a term used in a parent provisional patent application, the term used in the instant specification shall control.

As used herein "isolated" refers to material removed from its original environment and is thus altered "by the hand of man" from its natural state.

As used herein, "enriched" means to selectively concentrate or to increase the amount of one or more materials by elimination of the unwanted materials or selection and separation of desirable materials from a mixture (e.g., separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers. As used herein, the term "multipotent stem cells" are true stem cells but can only differentiate into a limited number of types. For example, the bone marrow contains multipotent stem cells that give rise to all the cells of the blood but may not be able to differentiate into other cells types.

By the term "animal-free" when referring to certain compositions, growth conditions, culture media, etc. described herein, is meant that no non-human animal-derived materials, such as bovine serum, proteins, lipids, carbohydrates, nucleic acids, vitamins, etc., are used in the preparation, growth, culturing, expansion, storage or formulation of the certain composition or process. By "no non-human animal-derived materials" is meant that the materials have never been in or in contact with a non-human animal body or substance so they are not xeno-contaminated. Generally, clinical grade materials, such as recombinantly produced human proteins, are used in the preparation, growth, culturing, expansion, storage and/or formulation of such compositions and/or processes.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50-fold and up to 150-fold higher than the number of cells in the primary culture after 5 passages, as compared to about a 20-fold increase in such cells using previous methods. In another example, the level of cells per gram of amniotic tissue in expanded compositions of AMP cells is at least 30-fold and up to 100-fold higher than the number of cells in the primary culture after 3 passages. Accordingly, an "expanded" population has at least a 2-fold, and up to a 10-fold, improvement in cell numbers per gram of amniotic tissue over previous methods. The term "expanded" is meant to cover only those situations in which a person has intervened to elevate the number of the cells.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to, hormones, cytokines, extracellular matrix (ECM), proteins, vesicles, antibodies, chemokines, receptors, inhibitors and granules. The medium containing the cellular factors is the conditioned medium. Examples of methods of preparing conditioned media have been described in U.S. Pat. No. 6,372,494 which is incorporated by reference in its entirety herein. As used herein, conditioned medium also refers to components, such as proteins, that are recovered and/or purified from conditioned medium or from for example, MSC cells.

As used herein, the term "mesenchymal stem cell composition" or "MSC composition" means conditioned medium that has been derived from MSCs and in some instances has undergone further processing. In some embodiments, "MSC secretome" can refer to the crude conditioned media derived from the MSC. In some embodiments, "MSC secretome" can refer to the composition obtained from the crude conditioned media after it has been subjected to further processing as described herein.

As used herein, the term "suspension" means a liquid containing dispersed components, e.g., cytokines. The dispersed components may be fully solubilized, partially solubilized, suspended or otherwise dispersed in the liquid. Suitable liquids include, but are not limited to, water, osmotic solutions such as salt and/or sugar solutions, cell culture media, and other aqueous or non-aqueous solutions. "Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions," can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene. Polynucleotides used herein can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the term "secretome composition" refers to a composition comprising one or more substances which are secreted from a cell. In certain embodiments, a secretome composition may include one or more cytokines, one or more exosomes, and/or one or more microvesicles. A secretome composition may be purified or unpurified. In some embodiments, a secretome composition may further comprise one or more substances that are not secreted from a cell (e.g., culture media, additives, nutrients, etc.). In some a secretome composition does not comprise and or comprises only trace amounts of one or more substances that are not secreted from a cell (e.g., culture media, additives, nutrients, etc.).

The terms "treatment," "treat," or "treating," and the like, as used herein covers any treatment of a human or nonhuman mammal (e.g., rodent, cat, dog, horse, cattle, sheep, and primates etc.), and includes preventing the disease or condition from occurring in a subject who may be predisposed to the disease or condition but has not yet been diagnosed as having it. It also includes inhibiting (arresting development of), relieving or ameliorating (causing regression of), or curing (permanently stopping development or progression) the disease, condition and/or any related symptoms. The terms "treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, e.g., arresting its development; (c) relieving and or ameliorating the disease or condition, e.g., causing regression of the disease or condition; or (d) curing the disease or condition, e.g., stopping its development or progression. The population of subjects treated by the methods of the invention includes subjects suffering from the undesirable condition or disease, as well as subjects at risk for development of the condition or disease. In some embodiments, "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder, and/or condition, and/or of a subject who exhibits only early signs of the disease, disorder, and/or condition. Alternatively and/or additionally, such treatment may be of a subject who exhibits one or more established signs of the relevant disease, disorder, and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

As used herein, a "wound" is any disruption, from whatever cause, of normal anatomy (internal and/or external anatomy) including but not limited to traumatic injuries such as mechanical (e.g. contusion, penetrating), thermal, chemical, electrical, radiation, concussive and incisional injuries; elective injuries such as operative surgery and resultant incisional hernias, fistulas, etc.; acute wounds, chronic wounds, infected wounds, and sterile wounds, as well as wounds associated with disease states (e.g. ocular contusion). A wound is dynamic and the process of healing is a continuum requiring a series of integrated and interrelated cellular processes that begin at the time of wounding and proceed beyond initial wound closure through arrival at a stable wound closure. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

As used herein, the terms "a" or "an" means one or more or at least one.

As used herein, a "therapeutically effective" or "effective" dosage or amount of a composition is an amount sufficient to have a positive effect on a given medical condition. If not immediate, the therapeutically effective or effective dosage or amount may, over period of time, provide a noticeable or measurable effect on a patient's health and well-being.

As used herein a "pharmaceutical composition" refers to an effective amount of the compositions described herein in combination with a delivery components. The pharmaceutical composition may optionally contain other components such as pharmaceutically suitable carriers and excipients, which may facilitate administration of a composition and/or its individual components to a subject.

The term "pharmaceutically acceptable carrier" refers to a carrier or a diluent that does not cause significant irritation to a subject and does not abrogate the biological activity and properties of the administered compounds.

The term "excipient" refers to an inert substance added to a pharmaceutical composition to further facilitate administration of a compound.

As used herein, the terms "mix", "mixing", and the like describe a mechanical process or a mechanical treatment of the components. For example, mixing can be in the sense of carrying out repeated cycles of pressing and folding or comparable processing steps which lead to an intense compression and mixing of the provided hydrophobic matrices.

Adult stem cells can be harvested from a variety of adult tissues, including bone marrow, fat, and dental pulp tissue. While all adult stem cells are cable of self-renewal and are considered multipotent, their therapeutic functions vary depending on their origin. As a result, each type of adult stem cell has unique characteristics that make them suitable for certain diseases. Mesenchymal stem cells (MSCs) are typically derived from the mesoderm and are multipotent, nonhematopoietic (non-blood) stem cells isolated from (derived from) capable of differentiating into a variety of tissues, including osteoblasts (e.g., bone cells), chondrocytes (e.g., cartilage cells), myocytes (e.g., muscle cells) and adipocytes (e.g., fat cells which give rise to marrow adipose tissue). As used herein, "isolated" refers to cells removed from their original environment. Stem cells produce factors, such as growth factors, that regulate or are important for regulating multiple biological processes. A growth factor is an agent, such as a naturally occurring substance capable of stimulating cellular growth and/or proliferation and/or cellular differentiation. Typically, growth factors are proteins or steroid hormones. While the terms "growth factor" and "factor" and the like are used interchangeably herein, the term "biological factor" is not limited to growth factors.

Human mesenchymal stem cells (MSCs), can be characterized by the surface marker profile of CD45−/CD31−/CD73+/CD90+/CD105+/CD44+ (or any suitable subset thereof). (See, Bourn et al., *Cytotherapy*, 15(6):641-648 (2013)). Further, appropriate stem cells display the CD34+ positive at the time of isolation, but lose this marker during culturing. Therefore, the full marker profile for one stem cell type that may be used according to the present application includes CD45−/CD31−/CD73+/CD90+/CD105+. In another embodiment utilizing mouse stem cells, the stem cells are characterized by the Sca-1 marker, instead of CD34, to define what appears to be a homologue to the human cells described above, with the remaining markers remaining the same.

The phrase "conditioned medium" or "CM" refers to media which includes biological factors secreted by MSCs. This can also be referred to herein as the "secretome", "MSC-CM", "MSC secretome" and/or "MSC derived secretome". Also provided are processed "conditioned medium" which included biological factors secreted by MSCs and which has been further processed by, for example, filtration, purification, and/or concentration procedures. The "conditioned medium" is obtained by culturing stem cells in media, as described herein in detail, and separating the resulting media, which contains stem cells and their secreted stem cell products (secretome) into conditioned medium that contains biological factors and fewer stem cells than were present prior to separation. The conditioned medium may be used in the methods described herein and is substantially free of stem cells (may contain a small percentage of stem cells) or free of stem cells. Biological factors that may be in the conditioned medium include, but are not limited to, proteins (e.g., cytokines, chemokines, growth factors, enzymes), nucleic acids (e.g., miRNA), lipids (e.g., phospholipids), polysaccharides, and/or combinations thereof. Any combination(s) of these biological factors may be either bound within or on the surface of extracellular vesicles (e.g., exosomes) or separate from extracellular vesicles.

B. Compositions and Formulations

The present invention meets this need by providing compositions comprising fibronectin, optionally one or more growth factors that are non-covalently attached to the fibronectin (FN), for use in such treatments, as well as methods for making such compositions.

In some embodiments, the FN is stem cell-derived.

In some embodiments, the FN is MSC-derived FN.

In some embodiments, the FN is MSC-secreted FN.

In some embodiments, the FN is cellular FN. In some embodiments, the cellular FN of the present invention is a mixture of alternative splicing variants/isoforms such as EDA, EDB and V+. In some embodiments, the cellular FN is EDA+. In some embodiments, the cellular FN is EDB+. In some embodiments, the cellular FN is EDA+ and EDB+. In some embodiments, cellular fibronectin is V+.

In some embodiments, the cellular FN is cellularly derived FN, and wherein the FN is non-covalently attached to one or more growth factors.

In some embodiments, the composition provided herein is obtained from a conditioned medium. In some embodiments, the conditioned medium is obtained from a culture of mesenchymal stem cells (MSCs).

In some embodiments, the composition comprising FN is derived from MSC secretome (including processed MSC secretome).

In some embodiments, compositions comprising conditioned medium comprising mesenchymal stem cell (MSC) secretome and/or mesenchymal stem cell (MSC) secretome (including processed MSC secretome) are provided herein.

In some embodiments, the FN composition comprises 0.1 ng/mL-150,000 ng/ML FN. In some embodiments, the FN composition comprises 0.1 ng/mL-140,000 ng/ML FN. In some embodiments, the FN composition comprises 0.1 ng/mL-130,000 ng/ML FN. In some embodiments, the FN composition comprises about 135,000 ng/ML FN. In some embodiments, the FN composition comprises 0.1 ng/mL-120,000 ng/ML FN. In some embodiments, the FN composition comprises 0.1 ng/mL-110,000 ng/ML FN. In some embodiments, the FN composition comprises 0.1 ng/mL-100,000 ng/ML FN. In some embodiments, the FN composition comprises 0.1 ng/mL-90,000 ng/ML FN. In some embodiments, the FN composition comprises 0.1 ng/mL-80,000 ng/ML FN. In some embodiments, the FN composition comprises 0.1 ng/mL-70,000 ng/ML FN. In some embodiments, the FN composition comprises 0.1 ng/mL-60,000 ng/ML FN. In some embodiments, the FN composition comprises 0.1 ng/mL-50,000 ng/ML FN. In some embodiments, the FN composition comprises 0.1 ng/mL-40,000 ng/ML FN. In some embodiments, the FN composition comprises 0.1 ng/mL-30,000 ng/ML FN. In some embodiments, the FN composition comprises 0.1 ng/mL-20,000 ng/ML FN. In some embodiments, the FN composition comprises 0.1 ng/mL-10,000 ng/ML FN. In some embodiments, the FN composition comprises 0.1 ng/mL-9,000 ng/ML FN. In some embodiments, the FN composition comprises 0.1 ng/mL-8,000 ng/ML FN. In some embodiments, the FN composition comprises 0.1 ng/mL-7,000 ng/ML FN. In some embodiments, the FN composition comprises 0.1 ng/mL-6,000 ng/ML FN. In some embodiments, the FN composition comprises 0.1 ng/mL-5,000 ng/ML FN. In some embodiments, the FN composition comprises 0.1 ng/mL-4,000 ng/ML FN. In some embodiments, the FN composition comprises 0.1 ng/mL-3,000 ng/ML FN. In some embodiments, the FN composition comprises 50 ng/mL-150,000 ng/ML FN. In some embodiments, the FN composition comprises 50 ng/mL-140,000 ng/ML FN. In some embodiments, the FN composition comprises 50 ng/mL-130,000 ng/ML FN. In some embodiments, the FN composition comprises about 135,000 ng/ML FN. In some embodiments, the FN composition comprises 50 ng/mL-120,000 ng/ML FN. In some embodiments, the FN composition comprises 50 ng/mL-110,000 ng/ML FN. In some embodiments, the FN composition comprises 50 ng/mL-100,000 ng/ML FN. In some embodiments, the FN composition comprises 50 ng/mL-90,000 ng/ML FN. In some embodiments, the FN composition comprises 50 ng/mL-80,000 ng/ML FN. In some embodiments, the FN composition comprises 50 ng/mL-70,000 ng/ML FN. In some embodiments, the FN composition comprises 50 ng/mL-60,000 ng/ML FN. In some embodiments, the FN composition comprises 50 ng/mL-50,000 ng/ML FN. In some embodiments, the FN composition comprises 50 ng/mL-40,000 ng/ML FN. In some embodiments, the FN composition comprises 50 ng/mL-30,000 ng/ML FN. In some embodiments, the FN composition comprises 50 ng/mL-20,000 ng/ML FN. In some embodiments, the FN composition comprises 50 ng/mL-10,000 ng/ML FN. In some embodiments, the FN composition comprises 50 ng/mL-9,000 ng/ML FN. In some embodiments, the FN composition comprises 50 ng/mL-8,000 ng/ML FN. In some embodiments, the FN composition comprises 50 ng/mL-7,000 ng/ML FN. In some embodiments, the FN composition comprises 50 ng/mL-6,000 ng/ML FN. In some embodiments, the FN composition comprises 50 ng/mL-5,000 ng/ML FN. In some embodiments, the FN composition comprises 50 ng/mL-4,000 ng/ML FN. In some embodiments, the FN composition comprises 50 ng/mL-3,000 ng/ML FN.

In some embodiments, the FN composition comprises 500 ng/mL-150,000 ng/ML FN. In some embodiments, the FN composition comprises 500 ng/mL-140,000 ng/ML FN. In some embodiments, the FN composition comprises 500 ng/mL-130,000 ng/ML FN. In some embodiments, the FN composition comprises about 135,000 ng/ML FN. In some embodiments, the FN composition comprises 500 ng/mL-120,000 ng/ML FN. In some embodiments, the FN composition comprises 500 ng/mL-110,000 ng/ML FN. In some embodiments, the FN composition comprises 500 ng/mL-100,000 ng/ML FN. In some embodiments, the FN composition comprises 500 ng/mL-90,000 ng/ML FN. In some embodiments, the FN composition comprises 500 ng/mL-80,000 ng/ML FN. In some embodiments, the FN composition comprises 500 ng/mL-70,000 ng/ML FN. In some embodiments, the FN composition comprises 500 ng/mL-60,000 ng/ML FN. In some embodiments, the FN composition comprises 500 ng/mL-50,000 ng/ML FN. In some embodiments, the FN composition comprises 500 ng/mL-40,000 ng/ML FN. In some embodiments, the FN composition comprises 500 ng/mL-30,000 ng/ML FN. In some embodiments, the FN composition comprises 500 ng/mL-20,000 ng/ML FN. In some embodiments, the FN composition comprises 500 ng/mL-10,000 ng/ML FN. In some embodiments, the FN composition comprises 500 ng/mL-9,000 ng/ML FN. In some embodiments, the FN composition comprises 500 ng/mL-8,000 ng/ML FN. In some embodiments, the FN composition comprises 500 ng/mL-7,000 ng/ML FN. In some embodiments, the FN composition comprises 500 ng/mL-6,000 ng/ML FN. In some embodiments, the FN composition comprises 500 ng/mL-5,000 ng/ML FN. In some embodiments, the FN composition comprises 500 ng/mL-4,000 ng/ML FN. In some embodiments, the FN composition comprises 500 ng/mL-3,000 ng/ML FN.

In some embodiments, the FN composition comprises 1000 ng/mL-150,000 ng/ML FN. In some embodiments, the FN composition comprises 1000 ng/mL-140,000 ng/ML FN. In some embodiments, the FN composition comprises 1000 ng/mL-130,000 ng/ML FN. In some embodiments, the FN composition comprises about 135,000 ng/ML FN. In some embodiments, the FN composition comprises 1000 ng/mL-120,000 ng/ML FN. In some embodiments, the FN composition comprises 1000 ng/mL-110,000 ng/ML FN. In some embodiments, the FN composition comprises 1000 ng/mL-100,000 ng/ML FN. In some embodiments, the FN composition comprises 1000 ng/mL-90,000 ng/ML FN. In some embodiments, the FN composition comprises 1000 ng/mL-80,000 ng/ML FN. In some embodiments, the FN composition comprises 1000 ng/mL-70,000 ng/ML FN. In some embodiments, the FN composition comprises 1000 ng/mL-60,000 ng/ML FN. In some embodiments, the FN composition comprises 1000 ng/mL-50,000 ng/ML FN. In some embodiments, the FN composition comprises 1000 ng/mL-40,000 ng/ML FN. In some embodiments, the FN composition comprises 1000 ng/mL-30,000 ng/ML FN. In some embodiments, the FN composition comprises 1000 ng/mL-20,000 ng/ML FN. In some embodiments, the FN composition comprises 1000 ng/mL-10,000 ng/ML FN. In some embodiments, the FN composition comprises 1000 ng/mL-9,000 ng/ML FN. In some embodiments, the FN composition comprises 1000 ng/mL-8,000 ng/ML FN. In some embodiments, the FN composition comprises 1000 ng/mL-7,000 ng/ML FN. In some embodiments, the FN composition comprises 1000 ng/mL-6,000 ng/ML FN. In some embodiments, the FN composition comprises 1000 ng/mL-5,000 ng/ML FN. In some embodiments, the FN composition comprises 1000 ng/mL-4,000 ng/ML FN. In some embodiments, the FN composition comprises 1000 ng/mL-3,000 ng/ML FN.

In some embodiments, the FN composition comprises 50-5000 ng/mL FN. In some embodiments, the FN composition comprises 50-4000 ng/mL FN. In some embodiments, the FN composition comprises 100-4000 ng/mL FN. In some embodiments, the FN composition comprises 150-3500 ng/mL FN.

In some embodiments, the FN composition comprises 1000-70,000 ng/mL FN. In some embodiments, the FN composition comprises 500-50,000 ng/mL FN. In some embodiments, the FN composition comprises 1000-40,000 ng/mL FN. In some embodiments, the FN composition comprises 1500-35,000 ng/mL FN.

In some embodiments, the FN composition comprises about 0.5-50 g/mL FN. In some embodiments, the FN composition comprises 5-45 ng/mL FN. In some embodiments, the FN composition comprises 10-40 ng/mL FN. In some embodiments, the FN composition comprises 15-35 ng/mL FN. In some embodiments, the FN composition comprises 20-30 ng/mL FN. In some embodiments, the cellular FN composition comprises about 25 ng/mL FN.

In some embodiments, the FN composition further comprises one or more growth factors. In some embodiments, the FN composition comprising one or more growth factors is derived from an MSC secretome. In some embodiments, the cellular FN in the composition is attached to one or more growth factors. In some embodiments, the FN are non-covalently attached to the one or more growth factors. In some embodiments, the one or more growth factors are selected from the group consisting of FGFs (such as FGF-2; also referred to as fibroblast growth factor-2), PDGF (also referred to as platelet-derived growth factor), HGF (also referred to as hepatocyte growth factor), VEGF, TGFβ1 (also referred to as TGFbeta1 or transforming growth factor β1), TGFβ2 (also referred to as TGFbeta2 or transforming growth factor β2), IGF-1 (also referred to as insulin growth factor 1), IGF-2 (also referred to as insulin growth factor 2), NGF (also referred to as nerve growth factor), neurotrophins, and EGF (also referred to as epidermal growth factor).

In some embodiments, the FN composition further comprises FGFs. In some embodiments, the FGF is FGF-2. In some embodiments, the FN composition further comprises FGF-2.

In some embodiments, the FN composition further comprises PDGF. In some embodiments, the composition further comprises at least about 0.1 ng/mL PDGF.

In some embodiments, the FN composition further comprises HGF. In some embodiments, the FN composition comprises 0.1-10 ng/mL, or 2.0+/−0.3 ng/mL HGF.

In some embodiments, the FN composition further comprises VEGF. In some embodiments, the VEGF is at a concentration of about 100-800 pg/mL, or 304+/−44 pg/mL.

In some embodiments, the FN composition further comprises TGFβ1.

In some embodiments, the FN composition further comprises TGFβ2.

In some embodiments, the FN composition further comprises IGF-1. IGF-2, and EGF.

In some embodiments, the FN composition further comprises IGF-2.

In some embodiments, the FN composition further comprises NGF.

In some embodiments, the FN composition further comprises neurotrophins.

In some embodiments, the FN composition further comprises EGF.

In some embodiments, the FN composition is formulated at a pH of about pH 4.5 to about pH 8. In some embodiments, the FN composition is formulated at a pH of about pH 4.7 to about pH 7.8. In some embodiments, the FN composition is formulated at a pH of about pH 5.0 to about pH 7.5. In some embodiments, the FN composition is formulated at a pH of about pH 5.5 to about pH 7.5. In some embodiments, the FN composition is formulated at a pH of about pH 6 to about pH 7.5.

In some embodiments, the FN composition is formulated at a pH of about pH 4.5, about pH 5.0, about pH 5.5, about pH 6.0, about pH 6.5, about pH 7.0, about pH 7.4, about pH 8.0. In some embodiments, the cellular FN composition is formulated at a pH of about pH 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0.

In some embodiments, the FN composition does not comprise certain components. In some embodiments, the FN composition does not comprise certain components found in cellular media. In some embodiments, the FN composition does not comprise one or more components selected from the group consisting of xenobiotic components (for example, animal serum); Phenol red; peptides and biomolecules <3 kDa; antibiotics; protein aggregates (for example, protein aggregates >200 nm); cells; cell debris (cell debris do not include exosomes/Extracellular Vesicles (EVs); for example, non-exosome, non-EV cell debris); hormones (for example, hormones include, but are not limited to insulin and/or hydrocortisone); and/or L-glutamine. In some embodiments, the FN composition does not comprise xenobiotic components. In some embodiments, the FN composition does not comprise Phenol red. In some embodiments, the FN composition does not comprise peptides and biomolecules <3 kDa. In some embodiments, the FN composition does not comprise antibiotics. In some embodiments, the FN composition does not comprise protein aggregates (for example, protein aggregates >200 nm). In some embodiments, the FN composition does not comprise cells. In some embodiments, the FN composition does not comprise cell debris (cell debris do not include exosomes/EVs; for example, non-exosome, non-EV cell debris). In some embodiments, the FN composition does not comprise hormones (for example, hormones include, but are not limited to insulin and/or hydrocortisone. In some embodiments, the FN composition does not comprise L-glutamine.

In some embodiments, the FN composition further comprises mannitol, lactose, sorbitol, xylitol, sucrose, trehalose, mannose, maltose, lactose, glucose, raffinose, cellobiose, gentiobiose, isomaltose, arabinose, glucosamine, fructose, dextrose, and/or combinations thereof. In some embodiments, the FN composition further comprises phosphate. In some embodiments, the phosphate source is sodium phosphate or potassium phosphate. In some embodiments, the phosphate source is sodium phosphate. In some embodiments, the phosphate source is potassium phosphate. In some embodiments, the FN composition further comprises mono/di-sodium phosphate, mannitol, and trehalose, wherein the composition has a pH of about pH 7.4.

In some embodiments, the FN composition can comprise one or more additional agents including but not limited to glycine, glycerol, sodium chloride, potassium chloride, and/or dextrose. In some embodiments, the FN composition can comprise one or more additional agents selected from the group consisting of glycine, glycerol, sodium chloride, potassium chloride, and dextrose. In some embodiments, the FN composition can comprise one or more additional agents selected from the group consisting of glycine and glycerol, and dextrose. In some embodiments, the FN composition can comprise one or more additional agents selected from the group consisting of sodium chloride and potassium chloride.

In some embodiments, the FN composition is formulated in a buffer system. In some embodiments, the FN composition is formulated in a buffer system including but not limited to di/mono sodium phosphate, sodium citrate/citric acid, boric acid/sodium citrate, boric acid/sodium tetraborate, and/or citric acid/disodium phosphate. In some embodiments, the FN composition is formulated in a buffer system selected from the group consisting of di/mono sodium phosphate, sodium citrate/citric acid, boric acid/sodium citrate, boric acid/sodium tetraborate, and/or citric acid/disodium phosphate. In some embodiments, the FN composition is formulated in a di/mono sodium phosphate buffer system. In some embodiments, the FN composition is formulated in sodium citrate/citric acid buffer system. In some embodiments, the FN composition is formulated in a boric acid/sodium citrate buffer system. In some embodiments, the FN composition is formulated in a boric acid/sodium tetraborate buffer system. In some embodiments, the FN composition is formulated in a citric acid/disodium phosphate buffer system.

In some embodiments, the phosphate source is sodium phosphate or potassium phosphate. In some embodiments, the phosphate source is sodium phosphate. In some embodiments, the phosphate source is potassium phosphate. In some embodiments, the cellular FN composition comprises di-sodium phosphate/citric acid, mannitol, and trehalose, wherein the composition has a pH of about pH 6.4.

In some embodiments, the cellular FN composition further comprises a tonicity adjusting or tonicity modifying agent. In some embodiments, tonicity adjusting or tonicity modifying agent includes but is not limited to NaCl, KCl, mannitol, dextrose, sucrose, sorbitol, and/or glycerin. In some embodiments, tonicity adjusting or tonicity modifying agent is selected from the group consisting of NaCl, KCl, mannitol, dextrose, sucrose, sorbitol, and/or glycerin.

In some embodiments, the FN composition further comprises an adhesive agent. In some embodiments, the FN composition further comprises an adhesive agent including but not limited to hypromellose, Poloxamer 407, Poloxamer 188, Poloxomer 237, Poloxomer 338, Hypromellose, (HPMC), HEC, polycarbophil, polyvinylpyrrolidone (PVP), PVA (polyvinyl alcohol, polyimide, sodium hyaluronate, gellan gum, poly(lactic acid-co-glycolic acid) (PLGA), polysiloxane, polyimide, carboxymethylcellulose (CMC), or hydroxypropyl methylcellulose (HPMC), hydroxy methyl cellulose, hydroxy ethyl cellulose, sodium carboxy methyl cellulose, fibrin glue, polyethyelene glycol, and GelCORE. In some embodiments, the adhesive agent is hypromellose. In some embodiments, the adhesive agent is fibrin glue. In some embodiments, the adhesive agent is a polyethyelene glycol. In some embodiments, the adhesive agent is GelCORE (see, Sani, et al., Science Advances, Vol. 5, no. 3 (2019)).

In some embodiments, the FN composition comprises (a) processed conditioned medium comprising an MSC secretome produced by any one of the methods described herein; and (b) a polymer. In some embodiments, the cellular FN composition comprises conditioned medium comprising the MSC secretome which is produced as described herein and a polymer. In some embodiments, the cellular FN composition comprises processed conditioned medium comprising the MSC secretome which is produced as described herein and a polymer. In some embodiments the polymer can be a biodegradable polymer from which the composition components can be released. In some embodiments, the polymer enables sustained (slow) release of the components.

In some embodiments, the FN compositions provided herein are in the form of a therapeutic bandage (e.g., a polymer impregnated with cellular FN composition). The therapeutic bandage may be configured as needed, depending on the application. In some embodiments, the bandage is in the form or a patch or is configured as mesh.

In some embodiments, the FN compositions exhibit bio-penetrance, for example, ocular penetration, corneal penetration, and/or corneal permeation. In some embodiments, the FN composition exhibits the ability to be absorbed by the eye. In some embodiments, the FN composition exhibits inherent bio-penetrance. In some embodiments, the FN composition exhibits excipient-enabled bio-penetrance. In some embodiments, the FN composition exhibits bio-penetrance due to upregulation of the smaller factors. In some embodiments, the FN composition exhibits bio-penetrance due to the presence of a biopreservative. In some embodiments, the FN composition exhibits bio-penetrance due to the presence of the biopreservative benzalkonium chloride.

In some embodiments, the FN compositions exhibit long half-life and/or have increased stability as compared to other treatments. In some embodiments, the cellular FN compositions as provided herein allow for an upregulation of proteins that are allow for increased stability of the MSC secretome. In some embodiments, the cellular FN compositions as provided herein allow for upregulating chaperone proteins to improve stability of other proteins in the MSC secretome.

In some embodiments, the FN compositions exhibit ultra-potency when administered to a subject in need thereof. In some embodiments, the FN compositions allow for therapeutic efficacy with one drop or one administration per day.

C. Methods of Producing/Manufacturing

In some embodiments, the cellular FN provided herein is secreted by cells into a conditioned medium. In some embodiments, the cells are stem cells such as mesenchymal stem cells. In some embodiments, the conditioned medium is further processed to remove undesired constituents in order to produce the cellular FN composition.

In some embodiments, the conditioned medium from which the cellular FN composition (and, thus, mesenchymal stem cell secreted factors) can be obtained from mesenchymal stem cells collected from the patient or individual to be treated (the patient in need thereof) or from another (donor) individual, such as a young and/or healthy donor and/or from mesenchymal stem cells obtained commercially. For example, MSC obtained from the individual to be treated (autologous stem cells) or from a donor (allogeneic stem cells), can be used to produce the conditioned medium described herein, which can then be further processed into a cellular FN composition as described herein.

According to the present invention, the method of making an mesenchymal stem cell (MSC) secretome comprising:
 i. culturing mesenchymal stem cells (MSCs) in a first culture media;
 ii. removing the first culture media from step (i) from the MSCs;
 iii. washing the MSCs in step (ii);
 iv. adding a second culture media and culturing for about 1-5 days;
 v. harvesting the second culture media from step (iv) as conditioned media; and
 vi. processing the conditioned media in step (v) into the MSC secretome composition as described herein.

In some embodiments, culturing can be performed using a bioreactor system for culturing cells. In some embodiments, culturing can be performed using a bioreactor system for culturing stem cells. In some embodiments, culturing can be performed using a bioreactor system for culturing mesenchymal stem cells. In some embodiments, culturing can be performed using a media mixing technology. In some embodiments, culturing can be performed using a PBS Vertical Wheel™ Mixing Technology (commercially available from PBS Biotech, Inc.).

In some embodiments, in step (iv) processing the conditioned media in step (v) into the secretome composition comprises:
 a) filtering the harvested conditioned media from step (v) to remove cell particulate;
 b) concentrating the filtered conditioned media from step (a); and
 c) buffer exchanging with the formulation buffer.

In some embodiments, step c) comprises buffer exchanging with a buffer system selected from the group consisting of di/mono sodium phosphate, sodium citrate/citric acid, boric acid/sodium citrate, boric acid/sodium tetraborate, and citric acid/disodium phosphate.

In some embodiments, the filtering step (a) comprises the use of a 0.45 µm filter, a 0.22 µm filter, 0.8 µm filter, and 0.65 micron, a low protein binding PVDF membranes, and/or PES (polyethersulfone). In some embodiments, the filtering step (a) comprises the use of a 0.45 µm filter. In some embodiments, the filtering step (a) comprises the use of a 0.22 µm filter. In some embodiments, the filtering step (a) comprises the use of 0.8 µm filter. In some embodiments, the filtering step (a) comprises the use of 0.65 micron. In some embodiments, the filtering step (a) comprises the use of low protein binding PVDF membranes. In some embodiments, the filtering step (a) comprises the use of PES (polyethersulfone).

In some embodiments, the concentration step (b) comprises using a hollow fiber filters, tangential flow filtration systems, or centrifugation based size exclusion techniques. In some embodiments, the concentration step (b) comprises using a hollow fiber filters technique. In some embodiments, the concentration step (b) comprises using a tangential flow filtration systems. In some embodiments, the concentration step (b) comprises using a centrifugation based size exclusion technique.

In some embodiments, the centrifugation based size exclusion techniques employs a 3-10 kDa MW cutoff. In some embodiments, the centrifugation based size exclusion techniques employs at least a 3 kDa MW cutoff, at least a 4 kDa MW cutoff, at least a 5 kDa MW cutoff, at least a 6 kDa MW cutoff, at least a 7 kDa MW cutoff, at least a 8 kDa MW cutoff, at least a 9 kDa MW cutoff, at least a 10 kDa MW cutoff, at least a 11 kDa MW cutoff, at least a 12 kDa MW cutoff, at least a 13 kDa MW cutoff, at least a 14 kDa MW cutoff, at least a 15 kDa MW cutoff, at least a 16 kDa MW cutoff, at least a 17 kDa MW cutoff, at least a 18 kDa MW cutoff, at least a 19 kDa MW cutoff, at least a 20 kDa MW cutoff, at least a 21 kDa MW cutoff, at least a 22 kDa MW cutoff, at least a 23 kDa MW cutoff, at least a 24 kDa MW cutoff, at least a 25 kDa MW cutoff, at least a 26 kDa MW cutoff, at least a 27 kDa MW cutoff, at least a 28 kDa MW cutoff, at least a 29 kDa MW cutoff, and/or at least a 30 kDa MW cutoff.

In some embodiments, the method produces an MSC secretome composition and/or formulation as described herein above. In some embodiments, the first and/or second culture medium are MSC Media and/or MSC-XF.

MSCs, or cells differentiated from MSCs, can be made to produce a conditioned media comprising the cellular FN and optionally other desired secretome components, e.g., which comprises desired cytokines and/or desired therapeutic properties as described herein. For example, the secretome can be produced from MSCs of a super donor cell line. The secretome can also be produced from MSCs obtained commercially. In come embodiments, allogeneic MSCs (and/or cells derived therefrom) and/or allogeneic MSC-derived secretome compositions can be prepared and stored for large groups of individuals. Allogeneic MSCs (and/or cells derived therefrom) and/or MSC-derived secretome compositions can be made in advance so that they are ready when people need them. In certain embodiments, MSCs (and/or cells derived therefrom) and/or MSC-derived secretome compositions can be processed to manufacture a more concentrated solution or composition (e.g., a mesenchymal stem cell derived secretome composition or MSC secretome composition as described herein).

In some embodiments, the initial culture medium and the first culture medium are different. In some embodiments, the initial culture medium and the first culture medium are the same. Non-limiting examples of cell culture medium or media useful in culturing MSCs to produce conditioned media comprising the MSC secretome according to the present invention include hMSC Media Booster XFM, hMSC High Performance Basal Media, Minimum Essential Medium Eagle (MEME), ADC-1, LPM (Bovine Serum Albumin-free), F10 (HAM), F12 (HAM), DCCM1, DCCM2, RPMI 1640, BGJ Medium (with and without Fitton-Jackson Modification), StemPro, MSCGro, Mesen-Cult, NutriStem, Basal Medium Eagle (BME—with the addition of Earle's salt base), Dulbecco's Modified Eagle Medium (DMEM—with or without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Alpha (MEM-alpha), Minimum Essential Medium Eagle (MEM-E—with Earle's salt base), Minimum Essential Medium Eagle (MEM-H—with Hank's salt base) and Minimum Essential Medium Eagle (MEM-NAA with non-essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the present invention is MEM-alpha. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62 72, edited by William B. Jakoby and Ira H. Pastan, published by Academic Press, Inc.

In some embodiments, the cell culture medium for mesenchymal stem cells can be a serum-free medium. In some embodiments, the cell culture medium for mesenchymal stem cells can be supplemented with serum. In some embodiments, the cell culture medium for mesenchymal stem cells can be supplemented human platelet lysate. In some embodiments, the serum can include fetal bovine serum (FBS). In some embodiments, the cell culture medium for mesenchymal stem cells can be supplemented with serum such as fetal serum of bovine or other species. In some embodiments, the cell culture medium for mesenchymal stem cells can be supplemented with other components to facilitate cell growth and/or promote cell health, such as mercaptoethanol and/or antibiotics. In some embodiments, the cell culture medium for mesenchymal stem cells is not supplemented with antibiotics.

In some embodiments, the oxygen percentage is varied to facilitate cell growth and/or promote cell health. In some embodiments, the oxygen is at 5%, 10%, 15%, 20%, or 25% volume to facilitate cell growth and/or promote cell health. In some embodiments, the mesenchymal stem cells are grown under partial oxygen pressure to facilitate cell growth and/or promote cell health. In some embodiments, the mesenchymal stem cells are grown under a low oxygen partial pressure environment to facilitate cell growth and/or promote cell health.

In one aspect, the present invention is directed to conditioned medium (CM) comprising biological factors secreted by mesenchymal stem cells, which can be referred to as conditioned media comprising the MSC secretome. The conditioned medium can be obtained by culturing mesenchymal stem cells in media, as described herein, and separating the resulting media, which contains mesenchymal stem cells and their secreted mesenchymal stem cell products (referred to as biological factors and/or the secretome) into the components parts of the conditioned medium contain the secretome and mesenchymal stem cells grown in the conditioned media. The conditioned medium once separated comprises the mesenchymal stem cell secretome and can be further processed and/or used according to the methods described herein and is substantially free of mesenchymal stem cells (may contain a small percentage of stem cells and/or trace amounts of stem cells) or free of mesenchymal stem cells. The MSC secretome comprises a variety of biological factors including hormones, cytokines, extracellular matrix, proteins, vesicles, antibodies, chemokines, receptors, inhibitor, and granules. As described herein, the conditioned medium or media (CM or conditioned media comprising the MSC secretome) comprising the MSC secretome can be further processed, producing concentrated, conditioned medium (pCM or concentrated MSC secretome).

In some embodiments, the conditioned media comprising the MSC secretome or concentrated MSC secretome is produced by culturing mesenchymal stem cells in culture medium, replacing culture medium in which the mesenchymal stem cells have been cultured. In some embodiments, the resultant conditioned media comprising the MSC secretome is harvested (collected), then processed to produce concentrated MSC secretome. In certain embodiments, processing of the harvested conditioned media comprising the MSC secretome includes removal of some, most, or essentially all of the medium, or removal of some, most, or essentially all of selected components of the conditioned medium.

In some embodiments, the harvested conditioned media comprising the MSC secretome is filtered to produce concentrated MSC secretome. In some embodiments, the harvested conditioned media comprising the MSC secretome is ultra-filtered to produce concentrated MSC secretome.

In one aspect, provided herein are methods of producing processed conditioned medium comprising cellular FN, comprising (a) culturing stem cells in a cell culture medium, thereby generating conditioned medium that comprises factors secreted by the mesenchymal stem cells (e.g., conditioned media comprising the mesenchymal stem cell secretome); (b) harvesting the conditioned medium thereby producing harvested conditioned medium (e.g., harvested mesenchymal stem cell secretome); and (c) filtering harvested conditioned medium (e.g., harvested mesenchymal stem cell secretome) to produce processed conditioned medium (mesenchymal stem cell secretome). In some embodiments, the stem cells of (a) are cultured (have been cultured) in growth medium prior to being cultured in growth factor-free medium. Thus, in some embodiments, the methods comprise: (a) culturing mesenchymal stem cells in a first growth medium; (b) replacing the first growth medium with a second growth medium and culturing the stem cells in the second growth medium, thereby generating conditioned media comprising the mesenchymal stem cell secretome; (c) harvesting the conditioned media comprising the mesenchymal stem cell secretome, thereby producing harvested conditioned medium comprising the mesenchymal stem cell secretome; and (d) filtering harvested conditioned medium to produce processed conditioned medium comprising the mesenchymal stem cell secretome.

In some embodiments, the stem cells are mesenchymal stem cells. Mesenchymal stem cells (MSCs) are multipotent (capable of differentiating into multiple, but not all, cell lineages) nonhematopoietic (non-blood) stem cells isolated from (derived from) a variety of adult tissues, including bone marrow and adipose tissue. In certain embodiments, the mesenchymal stem cells are isolated from bone marrow. "Isolated" refers to cells removed from their original environment. MSCs may differentiate into cells of mesodermal lineage, for example, adipocytes, osteoblasts, and chondrocytes. MSCs have a small cell body with few cell processes that are long and thin. The cell body contains a large, round nucleus with a prominent nucleolus, which is surrounded by finely dispersed chromatin particles, giving the nucleus a clear appearance. The remainder of the cell body contains a small amount of Golgi apparatus, rough endoplasmic reticulum, mitochondria, and polyribosomes. The cells, which are long and thin, are widely dispersed and the adjacent extracellular matrix is populated by a few reticular fibrils but is devoid of the other types of collagen fibrils [Brighton, et al. 1991 The Journal of Bone and Joint Surgery 73(6):832-47]. MSCs described herein may express the following molecular marker (protein molecule characteristic of plasma membrane of a cell or cell type) profiles: bone morphogenic protein receptor$^{"1"}$ (BMPR$^+$); CD34$^+$Sca1$^+$Lin$^-$"; CD44$^+$; c-kit$^+$; Sca-1$^+$; Thy-1$^+$; NOTCH3; JAG1; ITGA11. MSCs may also express other cell type-specific markers (see, the World Wide Web at stemcells.nih.gov; Kaltz, et al. 2010 Exp Cell Res October 1; 316(16):2609-17, incorporated herein by reference]. MSCs described herein may be identified based on colony-forming unit assays to detect the multipotent differentiation potential of the MSCs (to what cell types the MSCs give rise). However, cells that are somewhat differentiated (progenitor cells) can also be used.

i. FN Composition—Processing

In some embodiments, in order to produce the FN composition, the conditioned medium comprising the MSC secretome described herein can in some embodiments be collected and filtered and/or purified to remove cell particulate and/or other detrimental components. For example, as described above under step (v) harvesting the second culture media from step (iv) as conditioned media. The filtration membranes used herein may be selected from any of those known in the art having a suitable membrane and configuration, such that they are capable of retaining the desired MSC secretome components while allowing the cell particulate and/or other detrimental components pass through. Thus, one may employ any suitable membrane which permits the retention of cells under the fluid dynamic conditions selected whilst allowing the detrimental components to pass through for removal. In some embodiments, an upper limit of pore size of about 5 microns and a lower limit of about 0.1 microns would be suitable. In some embodiments, filtration can be performed using a micropore filter. In some embodiments, filtration can be performed using a 0.5 μm to a 0.2 μm filter. In some embodiments, filtration can be performed using a 0.5 μm, 0.45 μm, 0.4 μm, 0.35 μm, 0.3 μm, 0.25 μm, 0.22 μm and/or a 0.2 μm filter. In some embodiments, filtration can be performed using a 0.45 μm filter. In some embodiments, filtration can be performed using a 0.22 μm filter. In some embodiments, filtration/purification can be performed using a low protein binding polyvinylidene difluoride (PVDF) membranes. In some embodiments, filtration/purification can be performed using polyethersulfone (PES).

In some embodiments, the filtering is by ultra-filtration. In some embodiments, the conditioned medium is filtered using a filter size of 3 kD (to achieve purification, desalting, and concentration in the processed conditioned medium of molecules larger than the filter size). In some embodiments, a filter size of less than 3 kD is used to filter the conditioned medium, while in other embodiments a filter size of greater than 3 kD is used, depending on the application for which the processed conditioned medium is used. In other embodiments, ultra-filtration of harvested conditioned medium is carried out using a filter of a different pore size (e.g., 2 kD, <2 kD or >2 kD) selected to determine the size of components of the resulting processed conditioned medium comprising the MSC secretome.

In some embodiments, the detrimental components in the growth supporting media are removed by medium exchange, preferably via "cross-flow filtration". Cross-flow filtration refers to a mode of filtration where a suspension of MSC secretome cells flows substantially parallel to a filter which is permeable to a component of the suspension other than cells. The cross-flow filtration process is characterized by a set of fluid dynamic parameters including Re=Reynolds number, γw=wall shear rate, ΔP=pressure drop and TMP=transmembrane pressure. Re, γw and ΔP will depend on the geometry of the filtration system, flow conditions and fluid properties. Such cross-flow processes can, in some embodiments, include hollow fiber filtration systems as well. See, for example, U.S. Pat. No. 5,053,334, incorporated herein by reference in its entirety.

In some embodiments, the FN composition can be further subject to concentrated in the absence of filtration and/or after filtration. In some embodiments, the FN composition can be concentrated using hollow fiber tangential flow technology.

In some embodiments, the FN composition can be concentrated using centrifugation based size exclusion technique, for example, amicons and/or centricons can be employed during the centration step. In some embodiments, the size cutoff is a 3-10 kDa MW cutoff. In some embodiments, the molecular weight cutoff for use during centrifugation based size exclusion technique concentration methods is at least about 3 kDa, at least about 4 kDa, at least about 5 kDa, at least about 6 kDa, at least about 7 kDa, at least about 8 kDa, at least about 9 kDa, or at least about 10 kDa, or at least about 15 kDa, or at least about 20 kDa, or at least about 25 kDa, or at least about 30 kDa.

In some embodiments, the FN composition is concentrated about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, or about 100-fold. In some embodiments, the FN composition is concentrated about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, or about 100-fold as compared to the conditioned media prior to concentration.

In some embodiments, the FN composition is further buffer exchanged after the concentration step into the final formulation buffer. In some embodiments, the FN composition is further buffer exchanged after the concentration step into the final formulation buffer without an adhesive agent. In some embodiments, buffer exchange comprises altering the buffer components of the FN composition. In some embodiments, the FN composition is not diluted during the buffer exchange step. In some embodiments, the FN composition is diluted less than 1%, less than 5%, less than 10%, less than 15%, less than 20%, or less than 25% during the buffer exchange step.

In some embodiments, the FN composition is buffer exchanged after the concentration step such that all traces of culture media components are removed. In some embodiments, the FN composition is buffer exchanged after the concentration step such that less than about 25%, less than about 20%, less than about 15%, less than about 10%, less than about 5%, less than about 4%, less than about 3%, less than about 2%, or less than about 1% or about 0% of the culture media components remain.

ii. FN Composition—Formulating

In some embodiments, the FN composition comprises 0.1 ng/mL-150,000 ng/ML FN. In some embodiments, the FN composition comprises 0.1 ng/mL-140,000 ng/ML FN. In some embodiments, the FN composition comprises 0.1 ng/mL-130,000 ng/ML FN. In some embodiments, the FN composition comprises about 135,000 ng/ML FN. In some embodiments, the FN composition comprises 0.1 ng/mL-120,000 ng/ML FN. In some embodiments, the FN composition comprises 0.1 ng/mL-110,000 ng/ML FN. In some embodiments, the FN composition comprises 0.1 ng/mL-100,000 ng/ML FN. In some embodiments, the FN composition comprises 0.1 ng/mL-9,000 ng/ML FN. In some embodiments, the FN composition comprises 0.1 ng/mL-80,000 ng/ML FN. In some embodiments, the FN composition comprises 0.1 ng/mL-70,000 ng/ML FN. In some embodiments, the FN composition comprises 0.1 ng/mL-70,000 ng/ML FN. In some embodiments, the FN composition comprises 0.1 ng/mL-60,000 ng/ML FN. In some embodiments, the FN composition comprises 0.1 ng/mL-50,000 ng/ML FN. In some embodiments, the FN composition comprises 0.1 ng/mL-40,000 ng/ML FN. In some embodiments, the FN composition comprises 0.1 ng/mL-30,000 ng/ML FN. In some embodiments, the FN composition comprises 0.1 ng/mL-20,000 ng/ML FN. In some embodiments, the FN composition comprises 0.1 ng/mL-10,000 ng/ML FN. In some embodiments, the FN composition comprises 50-5000 ng/mL FN. In some embodiments, the FN composition comprises 100-4000 ng/mL FN. In some embodiments, the FN composition comprises 150-3500 ng/mL FN.

In some embodiments, the FN composition comprises 50 ng/mL-150,000 ng/ML FN. In some embodiments, the FN composition comprises 50 ng/mL-140,000 ng/ML FN. In some embodiments, the FN composition comprises 50 ng/mL-130,000 ng/ML FN. In some embodiments, the FN composition comprises about 135,000 ng/ML FN. In some embodiments, the FN composition comprises 50 ng/mL-120,000 ng/ML FN. In some embodiments, the FN composition comprises 50 ng/mL-110,000 ng/ML FN. In some embodiments, the FN composition comprises 50 ng/mL-100,000 ng/ML FN. In some embodiments, the FN composition comprises 50 ng/mL-90,000 ng/ML FN. In some embodiments, the FN composition comprises 50 ng/mL-80,000 ng/ML FN. In some embodiments, the FN composition comprises 50 ng/mL-70,000 ng/ML FN. In some embodiments, the FN composition comprises 50 ng/mL-60,000 ng/ML FN. In some embodiments, the FN composition comprises 50 ng/mL-50,000 ng/ML FN. In some embodiments, the FN composition comprises 50 ng/mL-40,000 ng/ML FN. In some embodiments, the FN composition comprises 50 ng/mL-30,000 ng/ML FN. In some embodiments, the FN composition comprises 50 ng/mL-20,000 ng/ML FN. In some embodiments, the FN composition comprises 50 ng/mL-10,000 ng/ML FN. In some embodiments, the FN composition comprises 50 ng/mL-9,000 ng/ML FN. In some embodiments, the FN composition comprises 50 ng/mL-8,000 ng/ML FN. In some embodiments, the FN composition comprises 50 ng/mL-7,000 ng/ML FN. In some embodiments, the FN composition comprises 50 ng/mL-6,000 ng/ML FN. In some embodiments, the FN composition comprises 50 ng/mL-5,000 ng/ML FN. In some embodiments, the FN composition comprises 50 ng/mL-4,000 ng/ML FN. In some embodiments, the FN composition comprises 50 ng/mL-3,000 ng/ML FN.

In some embodiments, the FN composition comprises 500 ng/mL-150,000 ng/ML FN. In some embodiments, the FN composition comprises 500 ng/mL-140,000 ng/ML FN. In some embodiments, the FN composition comprises 500 ng/mL-130,000 ng/ML FN. In some embodiments, the FN composition comprises about 135,000 ng/ML FN. In some embodiments, the FN composition comprises 500 ng/mL-120,000 ng/ML FN. In some embodiments, the FN composition comprises 500 ng/mL-110,000 ng/ML FN. In some embodiments, the FN composition comprises 500 ng/mL-100,000 ng/ML FN. In some embodiments, the FN composition comprises 500 ng/mL-90,000 ng/ML FN. In some embodiments, the FN composition comprises 500 ng/mL-80,000 ng/ML FN. In some embodiments, the FN composition comprises 500 ng/mL-70,000 ng/ML FN. In some embodiments, the FN composition comprises 500 ng/mL-60,000 ng/ML FN. In some embodiments, the FN composition comprises 500 ng/mL-50,000 ng/ML FN. In some embodiments, the FN composition comprises 500 ng/mL-40,000 ng/ML FN. In some embodiments, the FN composition comprises 500 ng/mL-30,000 ng/ML FN. In some embodiments, the FN composition comprises 500 ng/mL-20,000 ng/ML FN. In some embodiments, the FN composition comprises 500 ng/mL-10,000 ng/ML FN. In some embodiments, the FN composition comprises 500 ng/mL-9,000 ng/ML FN. In some embodiments, the FN composition comprises 500 ng/mL-8,000 ng/ML FN. In some embodiments, the FN composition comprises 500 ng/mL-7,000 ng/ML FN. In some embodiments, the FN composition comprises 500 ng/mL-6,000 ng/ML FN. In some embodiments, the FN composition comprises 500 ng/mL-5,000 ng/ML FN. In some embodiments, the FN composition comprises 500 ng/mL-4,000 ng/ML FN. In some embodiments, the FN composition comprises 500 ng/mL-3,000 ng/ML FN. In some embodiments, the FN composition comprises 1000 ng/mL-150,000 ng/ML FN. In some embodiments, the FN composition comprises 1000 ng/mL-140,000 ng/ML FN. In some embodiments, the FN composition comprises 1000 ng/mL-130,000 ng/ML FN. In some embodiments, the FN composition comprises about 135,000 ng/ML FN. In some embodiments, the FN composition comprises 1000 ng/mL-120,000 ng/ML FN. In some embodiments, the FN composition comprises 1000 ng/mL-110,000 ng/ML FN. In some embodiments, the FN composition comprises 1000 ng/mL-100,000 ng/ML FN. In some embodiments, the FN composition comprises 1000 ng/mL-90,000 ng/ML FN. In some embodiments, the FN composition comprises 1000 ng/mL-80,000 ng/ML FN. In some embodiments, the FN composition comprises 1000 ng/mL-70,000 ng/ML FN. In some embodiments, the FN composition comprises 1000 ng/mL-60,000 ng/ML FN. In some embodiments, the FN composition comprises 1000 ng/mL-50,000 ng/ML FN. In some embodiments, the FN composition comprises 1000 ng/mL-40,000 ng/ML FN. In some embodiments, the FN composition comprises 1000 ng/mL-30,000 ng/ML FN. In some embodiments, the FN composition comprises 1000 ng/mL-20,000 ng/ML FN. In some embodiments, the FN composition comprises 1000 ng/mL-10,000 ng/ML FN. In some embodiments, the FN composition comprises 1000 ng/mL-9,000 ng/ML FN. In some embodiments, the FN composition comprises 1000 ng/mL-8,000 ng/ML FN. In some embodiments, the FN composition comprises 1000 ng/mL-7,000 ng/ML FN. In some embodiments, the FN composition comprises 1000 ng/mL-6,000 ng/ML FN. In some embodiments, the FN composition comprises 1000 ng/mL-5,000 ng/ML FN. In some embodiments, the FN composition comprises 1000 ng/mL-4,000 ng/ML FN. In some embodiments, the FN composition comprises 1000 ng/mL-3,000 ng/ML FN.

In some embodiments, the FN composition comprises 1000-70,000 ng/mL FN. In some embodiments, the FN composition comprises 500-50,000 ng/mL FN. In some embodiments, the FN composition comprises 1000-40,000 ng/mL FN. In some embodiments, the FN composition comprises 1500-35,000 ng/mL FN.

In some embodiments, the FN composition comprises about 0.5-50 g/mL FN. In some embodiments, the FN composition comprises 5-45 ng/mL FN. In some embodiments, the FN composition comprises 10-40 ng/mL FN. In some embodiments, the FN composition comprises 15-35 ng/mL FN. In some embodiments, the FN composition comprises 20-30 ng/mL FN.

In some embodiments, the FN is at a concentration of any suitable values within the ranges provided above. In some embodiments, the FN composition comprises about 20 ng/mL FN. In some embodiments, the FN composition comprises about 21 ng/mL FN. In some embodiments, the FN composition comprises about 22 ng/mL FN. In some embodiments, the FN composition comprises about 23 ng/mL FN. In some embodiments, the FN composition comprises about 24 ng/mL FN. In some embodiments, the FN composition comprises about 25 ng/mL FN. In some embodiments, the FN composition comprises about 26 ng/mL FN. In some embodiments, the FN composition comprises about 27 ng/mL FN. In some embodiments, the FN composition comprises about 28 ng/mL FN. In some embodiments, the FN composition comprises about 29 ng/mL FN. In some embodiments, the FN composition comprises about 30 ng/mL FN. In some embodiments, the FN composition comprises about 25 ng/mL FN.

In some embodiments, the FN composition comprises about 0.5-20 ng/mL FN. In some embodiments, the FN composition comprises about 3-8 ng/mL FN. In some embodiments, the FN composition comprises about 3 ng/mL FN. In some embodiments, the FN composition comprises about 3.5 ng/mL FN. In some embodiments, the FN composition comprises 4 ng/mL FN. In some embodiments, the FN composition comprises about 4.5 ng/mL FN. In some embodiments, the FN composition comprises 5 ng/mL FN. In some embodiments, the FN composition comprises about 5.5 ng/mL FN. In some embodiments, the FN composition comprises 6 ng/mL FN. In some embodiments, the FN composition comprises about 6.5 ng/mL FN. In some embodiments, the FN composition comprises 7 ng/mL cellular FN. In some embodiments, the FN composition comprises about 7.5 ng/mL cellular FN. In some embodiments, the FN composition comprises about 8 ng/mL cellular FN.

In some embodiments, the FN composition is prepared in a formulation comprising about 2 mg-3 mg per mL of monobasic sodium phosphate. In some embodiments, the FN composition is prepared in a formulation comprising about 4% to 5% per mL of monobasic sodium phosphate.

In some embodiments, the FN composition is prepared in a formulation comprising about 11 mg-12 mg per mL of dibasic sodium phosphate. In some embodiments, the FN composition is prepared in a formulation comprising about 21.5% to 23% per mL of dibasic sodium phosphate.

In some embodiments, the FN composition is prepared in a formulation comprising about 11.5 mg-13 mg per mL of mannitol. In some embodiments, the FN composition is prepared in a formulation comprising about 23% to 25% per mL of mannitol.

In some embodiments, the FN composition is prepared in a formulation comprising about 23 mg-25 mg per mL of trehalose dihydrate. In some embodiments, the FN composition is prepared in a formulation comprising about 46% to 48% per mL of trehalose dihydrate.

In some embodiments, the FN composition is prepared in a formulation that does not comprise hypromellose. In some embodiments, the FN composition is prepared in a formulation that optionally comprises hypromellose. In some embodiments, the FN composition is prepared in a formulation comprising about 0.5 mg-2 mg per mL of hypromellose. In some embodiments, the FN composition is prepared in a formulation comprising about 1% to 3% per mL of hypromellose.

In some embodiments, the FN composition is prepared in a formulation comprising hydrochloric acid and/or sodium hydroxide. In some embodiments, the FN composition is prepared in a formulation comprising hydrochloric acid. In some embodiments, the FN composition is prepared in a formulation comprising sodium hydroxide. In some embodiments, the hydrochloric acid and/or sodium hydroxide is employed to obtain the desired pH.

In some embodiments, the formulation comprises NaCl. In some embodiments, the formulation does not comprise NaCl. In some embodiments, the formulation does not comprise detectable levels of NaCl. In some embodiments, the formulation comprises $MgCl_2$. In some embodiments, the formulation does not comprise $MgCl_2$. In some embodiments, the formulation does not comprise detectable levels of $MgCl_2$. In some embodiments, the formulation does not comprise either NaCl or $MgCl_2$. In some embodiments, the formulation does not comprise detectable levels of either NaCl or $MgCl_2$.

In some embodiments, the FN formulation is isotonic with tears, including for example naturally occurring as well as synthetic tears or tear-like solutions.

In some embodiments, the FN composition is prepared in a formulation comprising the components as provided in Table 1 below:

TABLE 1

FN formulation embodiment.

| Constituent Present | Amount per 1 mL of product |
| --- | --- |
| FN | 0.5-50 ng |
| Monobasic sodium phosphate | 2.28 mg |
| Dibasic sodium phosphate | 11.45 mg |
| Mannitol | 12.2 mg |
| Trehalose Dihydrate | 24 mg |
| Hypromellose | 1 mg |
| Hydrochloric acid and/or sodium hydroxide | adjust as required |

TABLE 2

FN formulation embodiment.

| Constituent Present | Amount per 1 mL of product |
| --- | --- |
| FN | 0.5-50 ng |
| Monobasic sodium phosphate | 1.31 mg |
| Dibasic sodium phosphate | 5.73 mg |
| Mannitol | 6.1 mg |
| Trehalose Dihydrate | 12 mg |
| Hypromellose | 0.5 mg |
| Hydrochloric acid and/or sodium hydroxide | adjust as required |

In some embodiments, the FN composition comprises:

| Constituent Present | Amount per 1 mL of product |
| --- | --- |
| FN | 0.5-50 ng |
| Monobasic sodium phosphate | 2.28 mg |
| Dibasic sodium phosphate | 11.45 mg |
| Mannitol | 12.2 mg |
| Trehalose Dihydrate | 24 mg |
| Hypromellose | 1 mg |

In some embodiments, the FN composition comprises:

| Constituent Present | Amount per 1 mL of product |
| --- | --- |
| FN | 0.5-50 ng |
| Monobasic sodium phosphate | 1.31 mg |
| Dibasic sodium phosphate | 5.73 mg |
| Mannitol | 6.1 mg |
| Trehalose Dihydrate | 12 mg |
| Hypromellose | 0.5 mg |

In some embodiments, the FN composition does not comprise NaCl and comprises:

| Constituent Present | Amount per 1 mL of product |
| --- | --- |
| FN | 0.5-50 ng |
| Monobasic sodium phosphate | 1.31 mg |
| Dibasic sodium phosphate | 5.73 mg |
| Mannitol | 6.1 mg |
| Trehalose Dihydrate | 12 mg |
| Hypromellose | 0.5 mg |

In some embodiments, the FN composition does not comprise $MgCl_2$ and comprises:

| Constituent Present | Amount per 1 mL of product |
| --- | --- |
| FN | 0.5-50 ng |
| Monobasic sodium phosphate | 1.31 mg |
| Dibasic sodium phosphate | 5.73 mg |
| Mannitol | 6.1 mg |
| Trehalose Dihydrate | 12 mg |
| Hypromellose | 0.5 mg |

In some embodiments, the FN composition does not comprise NaCl or $MgCl_2$ and comprises:

| Constituent Present | Amount per 1 mL of product |
| --- | --- |
| FN | 0.5-50 ng |
| Monobasic sodium phosphate | 1.31 mg |
| Dibasic sodium phosphate | 5.73 mg |
| Mannitol | 6.1 mg |
| Trehalose Dihydrate | 12 mg |
| Hypromellose | 0.5 mg |

In some embodiments, the FN composition comprises 0.5-50 ng/mL FN, 2.28 mg/mL monobasic sodium phosphate, 10-12 mg/mL dibasic sodium phosphate, 11-13 mg/mL mannitol, 2-25 mg/mL trehalose dihydrate, and 0.5-2 mg/mL Hypromellose. In some embodiments, the FN composition does not comprise NaCl and/or $MgCl_2$.

In some embodiments, the FN composition comprises 0.5-50 ng/mL FN, 2.28 mg/mL monobasic sodium phosphate, 11.45 mg/mL dibasic sodium phosphate, 12.2 mg/mL mannitol, 24 mg/mL trehalose dihydrate, and 1 mg/mL Hypromellose. In some embodiments, the FN composition does not comprise NaCl and/or $MgCl_2$.

In some embodiments, the FN composition comprises 0.5-50 ng/mL FN, 1.31 mg/mL monobasic sodium phosphate, 4.5-7 mg/mL dibasic sodium phosphate, 5.5-7.5 mg/mL mannitol, 11-13 mg/mL trehalose dihydrate, and 0.1-1.5 mg/mL Hypromellose. In some embodiments, the FN composition does not comprise NaCl and/or $MgCl_2$.

In some embodiments, the FN composition comprises 0.5-50 ng/mL FN, 1.31 mg/mL monobasic sodium phosphate, 5.73 mg/mL dibasic sodium phosphate, 6.1 mg/mL mannitol, 12 mg/mL trehalose dihydrate, and 0.5 mg/mL Hypromellose. In some embodiments, the FN composition does not comprise NaCl and/or $MgCl_2$.

D. Assay Methods/Therapeutic Properties

In some embodiments of the invention, the FN composition is processed to achieve certain ingredient ratios/concentrations as well as properties for the FN composition.

In some embodiments of the invention, the FN composition is processed to achieve certain potency performance criteria. In some embodiments, the buffer exchange step potentiates the potency of the FN composition.

Extracellular Vesicles are membrane bound particles that carry cargo of soluble and insoluble substances mentioned above. The term "Extracellular Vesicles" refers a group of secreted or shredded vesicles of various species. These are generally divided into the following subtypes: 1) microvesicles or Shed microvesicles which typically exhibit a size range of 50-1500 nm; 2) exosomes which typically exhibit a size range of 30-120 nm; and 3) vesicles which typically exhibit a size range of less than 500 nm (i.e., <500 nm). (See, for example, WO2019016799, incorporated by reference herein in its entirety.) In some embodiments, the FN composition can be analyzed for particle count and/or to quantitate the extracellular vesicles (EVs) present in the secretome.

In some embodiments, EVs are present in a concentration of about $2.5 \times 10^5$/uL, $2.6 \times 10^5$/uL, $2.7 \times 10^5$/uL, $2.8 \times 10^5$/uL, $2.9 \times 10^5$/uL, $3.0 \times 10^5$/uL, $3.1 \times 10^5$/uL, $3.2 \times 10^5$/uL, $3.3 \times 10^5$/uL, $3.4 \times 10^5$/uL, $3.5 \times 10^5$/uL, $3.6 \times 10^5$/uL, $3.7 \times 10^5$/uL, $3.8 \times 10^5$/uL, $3.9 \times 10^5$/uL, $4.0 \times 10^5$/uL, $4.1 \times 10^5$/uL, $4.2 \times 10^5$/uL, $4.3 \times 10^5$/uL, $4.4 \times 10^5$/uL, $4.5 \times 10^5$/uL, $4.6 \times 10^5$/uL, $4.7 \times 10^5$/uL, $4.8 \times 10^5$/uL, $4.9 \times 10^5$/uL, or about $5.0 \times 10^5$/uL. In some embodiments, EVs are present in a concentration of about $3.8 \times 10^5$/uL +/− $0.8 \times 10^5$.

In some embodiments, EVs are present in a concentration of about $2.5 \times 10^5$/uL, $2.6 \times 10^5$/uL, $2.7 \times 10^5$/uL, $2.8 \times 10^5$/uL, $2.9 \times 10^5$/uL, $3.0 \times 10^5$/uL, $3.1 \times 10^5$/uL, $3.2 \times 10^5$/uL, $3.3 \times 10^5$/uL, $3.4 \times 10^5$/uL, $3.5 \times 10^5$/uL, $3.6 \times 10^5$/uL, $3.7 \times 10^5$/uL, $3.8 \times 10^5$/uL, $3.9 \times 10^5$/uL, $4.0 \times 10^5$/uL, $4.1 \times 10^5$/uL, $4.2 \times 10^5$/uL, $4.3 \times 10^5$/uL, $4.4 \times 10^5$/uL, $4.5 \times 10^5$/uL, $4.6 \times 10^5$/uL, $4.7 \times 10^5$/uL, $4.8 \times 10^5$/uL, $4.9 \times 10^5$/uL, or about $5.0 \times 10^5$/uL and average 110-120 nm in diameter. In some embodiments, EVs are present in a concentration of about $2.5 \times 10^5$/uL, $2.6 \times 10^5$/uL, $2.7 \times 10^5$/uL, $2.8 \times 10^5$/uL, $2.9 \times 10^5$/uL, $3.0 \times 10^5$/uL, $3.1 \times 10^5$/uL, $3.2 \times 10^5$/uL, $3.3 \times 10^5$/uL, $3.4 \times 10^5$/uL, $3.5 \times 10^5$/uL, $3.6 \times 10^5$/uL, $3.7 \times 10^5$/uL, $3.8 \times 10^5$/uL, $3.9 \times 10^5$/uL, $4.0 \times 10^5$/uL, $4.1 \times 10^5$/uL, $4.2 \times 10^5$/uL, $4.3 \times 10^5$/uL, $4.4 \times 10^5$/uL, $4.5 \times 10^5$/uL, $4.6 \times 10^5$/uL, $4.7 \times 10^5$/uL, $4.8 \times 10^5$/uL, $4.9 \times 10^5$/uL, or about $5.0 \times 10^5$/uL and average 112-116 nm in diameter. In some embodiments, EVs are present in a concentration of about $2.5 \times 10^5$/uL, $2.6 \times 10^5$/uL, $2.7 \times 10^5$/uL, $2.8 \times 10^5$/uL, $2.9 \times 10^5$/uL, $3.0 \times 10^5$/uL, $3.1 \times 10^5$/uL, $3.2 \times 10^5$/uL, $3.3 \times 10^5$/uL, $3.4 \times 10^5$/uL, $3.5 \times 10^5$/uL, $3.6 \times 10^5$/uL, $3.7 \times 10^5$/uL, $3.8 \times 10^5$/uL, $3.9 \times 10^5$/uL, $4.0 \times 10^5$/uL, $4.1 \times 10^5$/uL, $4.2 \times 10^5$/uL, $4.3 \times 10^5$/uL, $4.4 \times 10^5$/uL, $4.5 \times 10^5$/uL, $4.6 \times 10^5$/uL, $4.7 \times 10^5$/uL, $4.8 \times 10^5$/uL, $4.9 \times 10^5$/uL, or about $5.0 \times 10^5$/uL and average 114 nm in diameter. In some embodiments, EVs are present in a concentration of about $3.8 \times 10^5$/uL +/− $0.8 \times 10^5$ and average 114 nm in diameter.

iii. FN Composition—Therapeutic Properties

In some embodiments, the FN composition of the present invention comprises cellular FN. In some embodiments, the FN composition comprises cellular FN. In some embodiments, the cellular FN of the present invention is a mixture of alternative splicing variants/isoforms such as EDA, EDB and V+. In some embodiments, the cellular FN is EDA+. In some embodiments, the cellular FN is EDB+. In some embodiments, the cellular FN is EDA+ and EDB+. In some embodiments, cellular fibronectin is V+.

In some embodiments, the FN composition of the present disclosure further comprises one or more growth factors.

In some embodiments, the FN composition of the present disclosure exhibits a variety of therapeutic properties, including for example, anti-angiogenic properties (blood vessels and/or lymphatic vessels), anti-fibrotic properties, anti-inflammatory properties, properties promoting cell migration, proliferation, cell adhesion, spreading, survival, and extracellular matrix (ECM) assembly and architecture, mitogenic promoting properties, anti-oxidative stress/damage properties.

In some embodiments, the FN composition exhibits anti-fibrotic properties. In some embodiments, such anti-fibrotic properties can be assayed for using standard assays. In some embodiments, the present of various factors and/or activities with regard to the FN composition are indicative of anti-fibrotic properties. In some embodiments, factors which are indicative of anti-fibrotic properties include one or more growth factors selected from the group consisting of FGFs (such as FGF-2), PDGF, HGF, VEGF, TGFβ1, TGFβ2, IGF-1, IGF-2, NGF, neurotrophins, and EGF.

In some embodiments, the FN composition exhibits anti-inflammatory properties. In some embodiments, the FN composition inhibits inflammation. In some embodiments, the FN composition inhibits inflammation by 5%, 10%, 15%, 20%, 30%, 40%, 50%, 60%, 70%, 80%. 90%, or 100% (e.g., complete reduction in inflammation). In some embodiments, the FN composition prevents degranulation of mast cells.

In some embodiments, the FN composition promotes cell migration and proliferation, including for example, mitogenic and motogenic activities. In some embodiments, the FN composition promotes mitogenic activities. In some embodiments, the FN composition promotes motogenic activities. In some embodiments, the FN composition further comprises one or more growth factors selected from the group consisting of FGFs (such as FGF-2), PDGF, HGF, VEGF, TGFβ1, TGFβ2, IGF-1, IGF-2, NGF, neurotrophins, and EGF, which provides for additional cell migration and proliferation activities of the FN composition.

In some embodiments, the FN composition further comprises FGFs such as FGF-2, which provides for additional cell migration and proliferation activities of the FN composition.

In some embodiments, the FN composition further comprises HGF, which provides for additional cell migration and proliferation activities of the FN composition.

In some embodiments, the FN composition further comprises anti-apoptotic agents, which provides for the cell migration and proliferation activities of the FN composition. In some embodiments, the FN composition comprises anti-apoptotic agents include but are not limited to FGF-2, HGF and IGF-1, and which provide for additional cell migration and proliferation activities of the FN composition. In some embodiments, the FN composition comprises anti-apoptotic agents selected from the group the consisting of FGF-2, HGF and IGF-1, and which provide for additional cell migration and proliferation activities of the FN composition.

iv. FN Composition—Biophysical/Biochemical Properties

Biochemical and Biophysical Characterization:

In some embodiments, the present invention provides methods for characterization of the FN composition. In some embodiments, the FN composition characterization will include: 1) a comprehensive and/or quantitative mapping of the molecular entities in the FN composition; 2) measuring the contributions of select factors to biological activity; and 3) measuring biophysical parameters. In some embodiments, in order to determine the properties of the FN composition, various potency assays can be performed on the FN composition as described herein. In some embodiments, the FN composition can be subjected to a comprehensive and/or quantitative mapping of the molecular entities in the FN composition; 2) measuring the contributions of select factors to biological activity; and 3) measuring biophysical parameters. In some embodiments, characterization assays include but are not limited to biophysical assays, biochemical assays, and bioassays. In some embodiments, characterization assays can include but are not limited to physical component characterizations, oxidative stress assays, safety analysis, stability assays, proliferation assays, migration assays, neovascularization assays, differentiation/scarring assays, inflammation assays, and/or an epithelial barrier integrity assays. In some embodiments, characterization assays are selected from the group consisting of physical component characterizations, oxidative stress assays, safety analysis, stability assays, proliferation assays, migration assays, neovascularization assays, differentiation/scarring assays, inflammation assays, and/or an epithelial barrier integrity assays.

Physical Component Characterizations:

In some embodiments, the characterization of the FN composition comprises a method employing a combination of bioanalytical techniques. In some embodiments, the characterization of the FN composition comprises determining the physical components of the FN composition. In some embodiments, characterization of the FN composition includes employing protein arrays, enzyme-linked immunosorbent assays (ELISAs), mass spectrometry, and immunoblotting. In some embodiments, the FN composition characterization can be used to identify the molecules in the FN composition. In some embodiments, protein arrays can be employed to identify factors in the FN composition. In some embodiments, mass spectrometry can be employed to determine the presence of one or more factors in the FN composition. In some embodiments, quantitative techniques can be employed to measure the levels of one or more factors. In some embodiments, quantitative techniques such as ELISA can be employed to measure the levels of each factor.

In some embodiments, the FN composition comprises cellular FN. In some embodiments, the cellular FN of the present invention is a mixture of alternative splicing variants/isoforms such as EDA, EDB and V+. In some embodiments, the cellular FN is EDA+. In some embodiments, the cellular FN is EDB+. In some embodiments, the cellular FN is EDA+ and EDB+. In some embodiments, cellular fibronectin is V+.

In some embodiments, the FN composition comprises the MSC secretome comprising protein factors and extracellular vesicles (EVs). In some embodiments, the cellular FN composition comprises trophic factors.

In some embodiments, the secretome comprises extracellular vesicles (EVs) in a size range of 30-200 nm and $1 \times 10^8$ to $5 \times 10^9$ EVs per mL.

In some embodiments, depletion studies can be performed to distill the individual contributions of critical factors. In some embodiments, using an antibody-based pulldown method, defined factors can be removed from the FN composition. In some embodiments, depletion can be verified by western blot and then evaluated by one or more bioassays, as described herein below. In some embodiments, depletion studies can be performed to evaluate the contributions of the protein fraction and the EV fraction.

Oxidative Stress:

In some embodiments, oxidative stress prevention assays can be performed on the FN composition. In some embodiments, the FN composition prevents corneal epithelium damage. In some embodiments, the cellular FN composition reduces the presence of inflammation. In some embodiments, the FN composition reduces the presence of inflammation as determined by an increase in the present of anti-inflammation markers. In some embodiments, the FN composition reduces the presence of inflammation as determined by an increase in the present of anti-inflammation markers, such as, for example, IL-8.

Safety Characterization:

In some embodiments, the FN composition can be evaluated for blood compatibility and implementing tests for sterility as well as pyrogen and endotoxin levels. In some embodiments, the FN composition can be evaluated blood compatibility. In some embodiments, evaluating blood compatibility includes assays for hemolysis and hemagglutination. In some embodiments, the FN composition does not exhibit detrimental effects with systemic exposure. In some embodiments, the FN composition does not exhibit detrimental effects with systemic exposure, such as with severe ocular burns. In some embodiments, the FN composition does not exhibit hemagglutination activity. In some embodiments, the FN composition does not induce hemolysis. In some embodiments, the FN composition does not induce hemolytic activity.

In some embodiments, the FN composition can be sterile such that it can be administered as part of a pharmaceutical formulation. In some embodiments, the FN composition can be free or substantially free of endotoxins. In some embodiments, the FN composition can be free or substantially free of microorganisms.

Stability:

In some embodiments, the biophysical characteristics of the FN composition can be evaluated and/or determined. In some embodiments, the fluorescence, static light scattering and dynamic light scatting to characterize protein stability metrics. In some embodiments, the following parameters can be measured to further characterize the secretome: thermal melting, thermal aggregation, Delta G, and/or viscosity. In some embodiments, a thermal melting assay is employed to determine FN composition stability. In some embodiments, a thermal aggregation assay is employed to determine FN composition stability. In some embodiments, delta G is employed as a measure for determining FN composition stability. In some embodiments, viscosity is measured as a FN composition characteristic. In some embodiments, viscosity is to determine FN composition stability.

In some embodiments, biophysical metrics can be employed to establish stability parameters for characterizing different FN composition formulations.

In some embodiments, the FN composition is stable at −20° C., 4° C., and room temperature (20° C.), for at least 7 days. In some embodiments, the FN composition is stable −20° C., 4° C., and room temperature (20° C.), for at least 14 days. In some embodiments, the FN composition is stable for at least 7 days, at least 1 week, at least 2 weeks, at least 3 weeks, or at least 1 month. In some embodiments, the FN composition is stable for at least 7 days, at least 14 days, at least 1 week, at least 2 weeks, at least 3 weeks, at least 1 month, at least 2 months, or at least 3 months at about −20° C. In some embodiments, the FN composition is stable for at least 7 days, at least 14 days, at least 1 week, at least 2 weeks, at least 3 weeks, or at least 1 month at about 4° C. In some embodiments, the FN composition is stable for at least 7 days, at least 14 days, at least 1 week, at least 2 weeks, at least 3 weeks, or at least 1 month at about 20° C. (or room temperature).

In some embodiments, the FN composition is stable for at least 7 days at about −20° C. In some embodiments, the FN composition is stable for at least 7 days at about 4° C. In some embodiments, the FN composition is stable for at least 7 days at about 20° C. In some embodiments, the FN composition is stable for at least 7 days at about 25° C. (room temperature).

In some embodiments, the FN composition is stable for at least 14 days at about −20° C. In some embodiments, the FN composition is stable for at least 14 days at about 4° C. In some embodiments, the FN composition is stable for at least 14 days at about 20° C. (or room temperature). In some embodiments, the FN composition is stable for at least 14 days at about 25° C. (room temperature).

Epithelial Barrier Integrity Assay

The corneal epithelium, more precisely, the apical surface of the epithelium has a major contribution to the overall barrier properties of the cornea and change to the corneal barrier serves as a sensitive factor for biocompatibility analysis. In some embodiments, the biophysical characteristics of the FN composition can be evaluated and/or determined such as by an epithelial barrier integrity assay. In some embodiments, the epithelial barrier integrity assay is a transepithelial electrical resistance (TEER). In some embodiments, the transepithelial electrical resistance (TEER) can be assessed to measure overall barrier properties. In some embodiments, 3D tissues can be transferred into 24-well plates containing 2 mL of TEER buffer and incubated for 10 min. In some embodiments, TEER can be measured using an epithelial volt-ohm meter EVOMÒ and the EndOhm-12 chamber (World Precision, Sarasota, FL). In some embodiments, at the end of the procedure, tissues can be used for tissue viability assessment using the following formula:

% Barrier integrity=100×[TEER (treated tissue)/ TEER (placebo control)]

In some embodiments, TEER can be employed to evaluate the effect on barrier integrity after topical application of the FN composition. In some embodiments, TEER can be employed to evaluate the effect on barrier integrity after topical application of the FN composition following corneal epithelial damage caused by topical exposure to nitrogen mustard (NM) utilizing the EpiCorneal tissue model (MatTek Corp). In some embodiments, FN composition can be applied topically, for example at 6 μg/mL (diluted in Placebo solution), as described in Example 6. In some embodiments, EpiCorneal tissues were cultured in 5 ml medium at standard culture conditions for 24 h.

Bioassays

In some embodiments, bioassays can be employed to characterize the FN composition. In some embodiments, bioassays can be related to corneal wound healing: epithelial cell migration and proliferation, stromal cell differentiation (e.g., scarring); neovascularization, and inflammation. In some embodiments, bioassays can be employed to evaluate the ability of the FN composition to mediate corneal wound healing: epithelial cell migration and proliferation, stromal cell differentiation (scarring); neovascularization; and inflammation. In some embodiments, the FN composition provided and assayed herein comprises cellular FN. In some embodiments, the cellular FN of the present invention is a mixture of alternative splicing variants/isoforms such as EDA, EDB and/or V+. In some embodiments, the cellular FN is EDA+. In some embodiments, the cellular FN is EDB+. In some embodiments, the cellular FN is EDA+ and EDB+. In some embodiments, cellular fibronectin is V+.

In some embodiments, the FN composition can be evaluated for the ability to promote wound healing such as ocular wound healing. In some embodiments, the FN composition can be evaluated for the ability to promote proliferation and migration. In some embodiments, the FN composition can be evaluated for the ability to promote proliferation. In some embodiments, the FN composition can be evaluated for the ability to promote migration.

In some embodiments, the FN composition comprises cellular FN. In some embodiments, the FN composition promotes proliferation and/or migration. In some embodiments, the FN composition promotes ocular wound healing. In some embodiments, the FN composition promotes proliferation. In some embodiments, the FN composition promotes migration. In some embodiments, the FN composition promotes cell adhesion. In some embodiments, the FN composition promotes cell spreading. In some embodiments, the FN composition promotes cell survival. In some embodiments, the FN composition promotes proper assembly and/or architecture of extracellular matrix (ECM). In some embodiments, the FN composition can be evaluated using a scratch assay to determine healing promoting ability. In some embodiments, the FN composition can be evaluated use a transwell migration assay to determine proliferation promoting ability. In some embodiments, the FN composition can be evaluated using a transwell migration assay to determine migration promoting ability.

Scratch Assay

In some embodiments, the assay of the present invention can include a "scratch assay" (also referred to as a "scratch wound assay", "scratch wound closure assay", "wound closure assay", or "wound healing assay"). In some embodiments, the FN composition promotes migration and this promotion of migration is determined and/or examined utilizing a "scratch assay". In some embodiments, the FN composition promotes proliferation and this promotion of proliferation is determined and/or examined utilizing a scratch assay. Generally, a scratch assay method is based on when artificial gap, also referred to as a "scratch", occurs on a confluent cell monolayer. The "scratch" can be monitored for the cells on the edge of the newly created gap migrating toward the opening to close/cover the "scratch". See, for example, Liang, C., Park, A. & Guan, J. *In vitro scratch assay: a convenient and inexpensive method for analysis of cell migration in vitro. Nat Protoc* 2, 329-333 (2007)). In some embodiments, the scratch assay is employed to screen for a candidate capable of inducing wound healing.

In one exemplary embodiment, the scratch assay provided herein comprises the following steps:
  (a) providing a layer of cells;
  (b) introducing a wound gap/scratch the layer of the cells; and
  (c) determining whether the wound gap heals/closes in the presence of the test composition, wherein the composition is administered to the cells either before or after the step (b); wherein closure of the wound gap is indicative of the ability of the test composition to induce ocular wound healing.

In some embodiments, the scratch assay is employed to corneal cells. In some embodiments, the cells assayed are mammalian cells. In some embodiments, the cells assayed are human cells. In some embodiments, the scratch assay is employed to retinal cells. In some embodiments, the scratch assay is employed to epithelial cell. In some embodiments, the scratch assay is employed to keratocyte. In some embodiments, the scratch assay is employed to fibroblast. In some embodiments, the scratch assay is employed to optic neuronal cells. In some embodiments, the scratch assay is employed to Ganglion cells. In some embodiments, the scratch assay is employed to retinal pigment epithelial cells. In some embodiments, the scratch assay is employed to retinal pigment epithelial cells. In some embodiments, the scratch assay is employed to lens epithelial cells. In some embodiments, the scratch assay is employed to iris pigment epithelial cells. In some embodiments, the scratch assay is employed to conjunctival fibroblasts. In some embodiments, the scratch assay is employed to non-pigmented ciliary epithelial cells. In some embodiments, the scratch assay is employed to trabecular meshwork cells. In some embodiments, the scratch assay is employed to ocular choroid fibroblasts. In some embodiments, the scratch assay is employed to conjunctival epithelial cells.

In some embodiments, the cells assayed form a confluent layer at the time one or more scratch (also referred to as "gap" or "wound") is introduced. In some embodiments, the confluent layer of the cells assayed is a monolayer.

In some embodiments, one or more scratches are introduced to the cells. In some embodiments, a single scratch is introduced. In some embodiments, multiple scratches are introduced to the cells. In some embodiments, one or more scratches are chemically introduced to the cells. In some embodiments, one or more scratches are introduced to the cells via chemical burn. In some embodiments, one or more scratches are introduced via an off-the-shelf drug or chemical compound. In one exemplary embodiment, the chemical burn is alkaline burn. In another exemplary embodiment, the chemical burn is nitrogen mustard gas burn. In some embodiments, one or more scratches are introducing to the cells by mechanically disrupting the layer of the cells. In some embodiments, one or more scratches are introduced by heat shock. In some embodiments, one or more scratches are introduced via laser pulses.

In some embodiments, the scratches introduced to the cells include a linear scratch. In some embodiments, the scratches introduced to the cells include crosshatched scratches. In some embodiments, the scratches introduced to the cells include a circular scratch. In some embodiments, the scratches introduced to the cells include a zigzag scratch. In some embodiments, the scratches introduced to the cells include a combination of the one or more aforementioned shapes.

In some embodiments, the scratch introduced is about 0.01 mm to 10 mm in size (i.e., the traverse length of separate migrating fronts of the wound/scratch on either side). In some embodiments, the scratch is about 0.01 mm to 0.1 mm, 0.1 mm to 1 mm, 1 mm to 10 mm, or any suitable value within these ranges, in size.

In some embodiments, a test reagent/composition is administered to the cells after one or more scratches are introduced. In some embodiments, a test reagent/composition is administered to the cells before one or more scratches are introduced. In some embodiments, the test reagent/composition is the FN composition. In some embodiments, the test reagent/composition is a conditional media. In some embodiments, the test reagent/composition is a biopolymer such as a protein. In some embodiments, the test reagent/composition is a pharmaceutical composition of one or more active compounds. In some embodiments, the test reagent/composition is screened for its ability to promote ocular wound healing.

In some embodiments, the test reagent/composition is concentrated before administration to the cells. In some embodiments, the test reagent/composition is diluted before being administered to the cells. In some embodiments, the test reagent/composition undergoes purification such as buffer exchange before being administered to the cells. In some embodiments, the test reagent/composition is lyophilized before being administered to the cells. In some embodiments, the test reagent/composition administered to the cells comprises about 10-100 μg/mL active components. In some embodiments, the test reagent/composition administered to the cells comprises about 10-100 μg/mL proteins. In some embodiments, the test reagent/composition administered to the cells comprises about 10-90 μg/mL proteins. In some embodiments, the test reagent/composition administered to the cells comprises about 20-80 μg/mL proteins. In some embodiments, the test reagent/composition administered to the cells comprises about 30-70 μg/mL proteins. In some embodiments, the test reagent/composition administered to the cells comprises about 40-60 μg/mL proteins. In some embodiments, the test reagent/composition administered to the cells comprises about 45 μg/mL proteins. In some embodiments, the test reagent/composition administered to the cells comprises about 50 μg/mL proteins. In some embodiments, the test reagent/composition administered to the cells comprises about 55 μg/mL proteins.

In some embodiments, the closure of one or more scratches is indicative of the ability of the test reagent to promote ocular wound healing. In some embodiments, the closure of one or more scratches is indicative of the ability of the test reagent to promote cell proliferation. In some embodiments, the closure of one or more scratches is indicative of the ability of the test reagent to promote cell migration. In some embodiments, the closure of a scratch is characterized as total number of cells migrated into the scratch. In some embodiments, the total number of cells migrated into the scratch is measured by physical counting (image analysis software) with or without staining (colorimetric or fluorometric). In some embodiments, the total number of cells migrated into the scratch is measured by absorbance or fluorometric based methods to spectroscopically quantitate the cell mass in the scratch. In some embodiments, the closure of a scratch is characterized as a percentage of the wound closure or a mathematically variant thereof, i.e., initial surface area of the wound minus remaining scratch surface area at a certain time then divided by the initial surface area of the scratch. In some embodiments, the closure of a scratch is characterized as a percentage of the remaining scratch area, i.e., a reciprocal of the percentage of the wound closure. In some embodiments, the closure of a scratch is characterized as the size of the scratch (i.e., traverse length of separate migrating fronts of the wound on either side). In some embodiments, image analysis software is employed to establish migrating scratch front (or boundary) and to measure the distance (in pixels, um, etc.) of the scratch remaining. In some embodiments, the closure of a scratch is characterized as the surface are of the scratch. In some embodiments, the surface area of the scratch (e.g., pixel^2 or μm^2) is determined by image analysis software. In some embodiments, the closure of a scratch is characterized as a temporal function. In some embodiments, the closure of a scratch is characterized as the time required for closure of all or a percentage of the scratch (e.g., 50%). In some embodiments, the closure of a scratch is characterized as a rate, such as cell free surface area of the scratch as a function of time. In some embodiments, the rate measured is the distance of cell migration/migration time.

In some embodiments, the closure of one or more scratches is measured for about 1 to 5 days. In some embodiments, the closure of one or more scratches is measured for about 2 to 4 days. In some embodiments, the closure of one or more scratches is measured for about 2 to 3 days. In some embodiments, the closure of one or more scratches is measured for about 2 days. In some embodiments, the closure of one or more scratches is measured for about 3 days. In some embodiments, the closure of one or more scratches is measured at a regular interval. In some embodiments, the closure of one or more scratches is measured daily. In some embodiments, the closure of one or more scratches is measured continuously.

In some embodiments, the FN composition of the present invention induces ocular wound healing in the scratch assay provided herein. In some embodiments, the FN composition induces ocular wound healing in the scratch assay provided herein. In some embodiments, the FN composition of the present invention increases wound closure in the scratch assay by at least 1-fold, 2-fold, 3-fold, 4-fold, 5-fold, 6-fold, 7-fold, 8-fold, 9-fold, 10-fold or more. In some embodiments, the FN composition of the present invention increases wound closure in the scratch assay by at least 1-fold. In some embodiments, the FN composition of the present invention increases wound closure in the scratch assay by at least 2-fold. In some embodiments, the FN composition of the present invention increases wound closure in the scratch assay by at least 3-fold. In some embodiments, the FN composition of the present invention increases wound closure in the scratch assay by at least 4-fold. In some embodiments, the FN composition of the present invention increases wound closure in the scratch assay by at least 5-fold. In some embodiments, the FN composition of the present invention increases wound closure in the scratch assay by at least 6-fold. In some embodiments, the FN composition of the present invention increases wound closure in the scratch assay by at least 7-fold. In some embodiments, the FN composition of the present invention increases wound closure in the scratch assay by at least 8-fold. In some embodiments, the FN composition of the present invention increases wound closure in the scratch assay by at least 9-fold. In some embodiments, the FN composition of the present invention increases wound closure in the scratch assay by at least 10-fold. In some embodiments, the FN composition of the present invention increases wound closure in the scratch assay by at least 10%, 20%, 30%, 40%, 50%, 60%, 70%, 80%, 90%, 100%, or more. In some embodiments, the FN composition of the present invention increases wound closure in the scratch assay by at least 10%. In some embodiments, the FN composition of the present invention increases wound closure in the scratch assay by at least 20%. In some embodiments, the FN composition of the present invention increases wound closure in the scratch assay by at least 30%. In some embodiments, the FN composition of the present invention increases wound closure in the scratch assay by at least 40%. In some embodiments, the FN composition of the present invention increases wound closure in the scratch assay by at least 50%. In some embodiments, the FN composition of the present invention increases wound closure in the scratch assay by at least 60%. In some embodiments, the FN composition of the present invention increases wound closure in the scratch assay by at least 70%. In some embodiments, the FN composition of the present invention increases wound closure in the scratch assay by at least 80%. In some embodiments, the FN composition of the present invention increases wound closure in the scratch assay by at least 90%. In some embodiments, the FN composition of the present invention increases wound closure in the scratch assay by at least 100%.

In some embodiments, the FN composition of the present invention induces ocular wound healing in the scratch assay provided herein. In some embodiments, the FN composition induces ocular wound healing in the scratch assay provided herein. In some embodiments, the FN composition increases wound closure in the scratch assay by at least 1-fold, 2-fold, 3-fold, 4-fold, 5-fold, 6-fold, 7-fold, 8-fold, 9-fold, 10-fold or more. In some embodiments, the FN composition increases wound closure in the scratch assay by at least 1-fold. In some embodiments, the FN composition increases wound closure in the scratch assay by at least 2-fold. In some embodiments, FN composition increases wound closure in the scratch assay by at least 3-fold. In some embodiments, FN composition increases wound closure in the scratch assay by at least 4-fold. In some embodiments, FN composition increases wound closure in the scratch assay by at least 5-fold. In some embodiments, FN composition increases wound closure in the scratch assay by at least 6-fold. In some embodiments, FN composition increases wound closure in the scratch assay by at least 7-fold. In some embodiments, FN composition increases wound closure in the scratch assay by at least 8-fold. In some embodiments, FN composition increases wound closure in the scratch assay by at least 9-fold. In some embodiments, FN composition increases wound closure in the scratch assay by at least 10-fold. In some embodiments, FN composition increases wound closure in the scratch assay by at least 10%, 20%, 30%, 40%, 50%, 60%, 70%, 80%, 90%, 100%, or more. In some embodiments, FN composition increases wound closure in the scratch assay by at least 10%. In some embodiments, FN composition increases wound closure in the scratch assay by at least 20%. In some embodiments, FN composition increases wound closure in the scratch assay by at least 30%. In some embodiments, FN composition increases wound closure in the scratch assay by at least 40%. In some embodiments, FN composition increases wound closure in the scratch assay by at least 50%. In some embodiments, FN composition increases wound closure in the scratch assay by at least 60%. In some embodiments, FN composition increases wound closure in the scratch assay by at least 70%. In some embodiments, FN composition increases wound closure in the scratch assay by at least 80%. In some embodiments, FN composition increases wound closure in the scratch assay by at least 90%. In some embodiments, FN composition increases wound closure in the scratch assay by at least 100%.

In some embodiments, at least 30 µg/mL of the test reagent is required to effect ocular wound healing in the scratch assay as provided herein. In some embodiments, at least 35 µg/mL of the test reagent is required to effect ocular wound healing in the scratch assay as provided herein. In some embodiments, at least 40 µg/mL of the test reagent is required to effect ocular wound healing in the scratch assay as provided herein. In some embodiments, at least 45 µg/mL of the test reagent is required to effect ocular wound healing in the scratch assay as provided herein. In some embodiments, at least 50 µg/mL of the test reagent is required to effect ocular wound healing in the scratch assay as provided herein.

In some embodiments, the test reagent is FN. In some embodiments, the FN is cellular FN.

Transwell Migration Assay

In some embodiments, the assays of the present invention include a "transwell migration assay" (also referred to as a "transwell cell invasion assay" or "transwell assay"). In some embodiments, the transwell migration assay is utilized to evaluate the ability of a candidate reagent to cell migration and/or proliferation. In some embodiments, the transwell migration assay is utilized to evaluate the ability of a candidate reagent to cell migration. In some embodiments, the transwell migration assay is utilized to evaluate the ability of a candidate reagent to cell proliferation. In some embodiments, the transwell migration assay is utilized to screen for a candidate capable of inducing cell migration/proliferation.

In one exemplary embodiment, the transwell migration assay provided herein comprises the step of the following:
(a) adding cells to an upper chamber comprising a membrane with pores, wherein the cells are supplemented with a basal medium in the absence of the test reagent/composition;
(b) placing the upper chamber into a container comprising the test reagent/composition, wherein the corneal cells in the upper chamber are separated from the test reagent/composition in the container by the membrane with pores;
(c) incubating the cells; and
(d) measuring/quantifying the cells that migrate through the membrane as indicative of the ability of the test reagent/composition to induce migration and/or proliferation of the cells.

In some embodiments, the transwell migration assay is employed to corneal cells. In some embodiments, the transwell migration assay is employed to retinal cells. In some embodiments, the transwell migration assay is employed to epithelial cell. In some embodiments, the transwell migration assay is employed to keratocyte. In some embodiments, the transwell migration assay is employed to fibroblast. In some embodiments, the transwell migration assay is employed to optic neuronal cells. In some embodiments, the transwell migration assay is employed to Ganglion cells. In some embodiments, the transwell migration assay is employed to retinal pigment epithelial cells. In some embodiments, the transwell migration assay is employed to retinal pigment epithelial cells. In some embodiments, the transwell migration assay is employed to lens epithelial cells. In some embodiments, the transwell migration assay is employed to iris pigment epithelial cells. In some embodiments, the transwell migration assay is employed to conjunctival fibroblasts. In some embodiments, the transwell migration assay is employed to non-pigmented ciliary epithelial cells. In some embodiments, the transwell migration assay is employed to trabecular meshwork cells. In some embodiments, the transwell migration assay is employed to ocular choroid fibroblasts. In some embodiments, the transwell migration assay is employed to conjunctival epithelial cells.

In some embodiments, the upper chamber of the transwell migration assay is sealed by a membrane with pores. In some embodiments, the upper chamber is a glass chamber. In some embodiments, the upper chamber is a plastic chamber. In some embodiments, the upper chamber is a Boyden chamber.

In some embodiments, the membrane of the upper chamber is a polycarbonate membrane with defined pore sizes. In some embodiments, the membrane is a basement membrane. In some embodiments, the average pore size of the membrane is less than the size of the cell assayed. In some embodiments, the average pore size of the membrane is about 1 to 15 µm. In some embodiments, the average pore size of the membrane is about 3 µm. In some embodiments, the average pore size of the membrane is about 5 µm. In some embodiments, the average pore size of the membrane is about 8 µm. In some embodiments, the average pore size of the membrane is about 12 µm.

In some embodiments, the membrane of the upper chamber is pre-treated. IN some embodiments, the membrane is pre-coated with one or more compounds or biopolymers enhancing cell adhesion and/or proliferation. In some embodiments, the membrane is pre-coated with extracellular matrix. In some embodiments, the membrane is pre-coated with collagen. In some embodiments, the membrane is pre-coated with fibronectin. In some embodiments, the membrane is pre-coated with laminin.

In some embodiments, the cells are added to the upper chamber comprising a basal cell culture medium. In some embodiments, the basal cell culture medium in the upper chamber is free from serum. Non-limiting examples of the cell culture medium include hMSC Media Booster XFM, hMSC High Performance Basal Media, Minimum Essential Medium Eagle (MEME), ADC-1, LPM (Bovine Serum Albumin-free), F10 (HAM), F12 (HAM), DCCM1, DCCM2, RPMI 1640, BGJ Medium (with and without Fitton-Jackson Modification), StemPro, MSCGro, MesenCult, NutriStem, Basal Medium Eagle (BME—with the addition of Earle's salt base), Dulbecco's Modified Eagle Medium (DMEM—with or without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Alpha (MEM-alpha), Minimum Essential Medium Eagle (MEM-E—with Earle's salt base), Minimum Essential Medium Eagle (MEM-H—with Hank's salt base) and Minimum Essential Medium Eagle (MEM-NAA with nonessential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. An exemplary medium for use in the present invention is MEM-alpha. In some embodiments, the cells assayed are added to an upper chamber comprising a gel. In some embodiments, the gel comprises biometrix such as extracellular matrix.

In some embodiments, the upper chamber is suspended in a container comprising one or more test reagents/compositions. In some embodiments, the upper chamber and container comprise the same compositions except for one or more test reagents/compositions. In other embodiments, the upper chamber and container comprise different compositions besides one or more test reagents/compositions. In some embodiments, the container further comprises one or more growth factors.

In some embodiments, the container is a reaction vessel. In some embodiments, the container is a well in a multi-well plate. In some embodiments, the container is a well in a multi-well plate such as 6-well plate, 12-well plate, 24-well plate, 48-well plate, or 96-well plate.

In some embodiments, the test reagent/composition as provided herein comprises a chemoattractant for the assayed cells. In some embodiments, the test reagent/composition comprises the FN composition. In some embodiments, the test reagent/composition comprises a conditional medium. In some embodiments, the test reagent/composition comprises a biopolymer such as a protein. In some embodiments, the test reagent/composition comprises a pharmaceutical composition of one or more active compounds. In some embodiments, the test reagent/composition is screened for its ability to promote cell migration and/or proliferation.

In some embodiments, the test reagent/composition is present in only the container and excluded from the upper chamber. In some embodiments, the test reagent/composition is present in both the upper chamber and container. In one exemplary embodiment, an increasing concentration gradient of the test reagent/composition from the upper chamber towards the container is present.

In some embodiments, the test reagent/composition is concentrated before being added. In some embodiments, the test reagent/composition is diluted before being added. In some embodiments, the test reagent/composition undergoes purification such as buffer exchange before being added. In some embodiments, the test reagent/composition is lyophilized before being added. In some embodiments, the test reagent/composition in the container comprises about 10-100 µg/mL active components. In some embodiments, the test reagent/composition in the container comprises about 10-100 µg/mL proteins. In some embodiments, the test reagent/composition in the container comprises about 10-90 µg/mL proteins. In some embodiments, the test reagent/composition in the container comprises about 20-80 µg/mL proteins. In some embodiments, the test reagent/composition in the container comprises about 30-70 µg/mL proteins. In some embodiments, the test reagent/composition in the container comprises about 40-60 µg/mL proteins. In some embodiments, the test reagent/composition in the container comprises about 45 µg/mL proteins. In some embodiments, the test reagent/composition in the container comprises about 50 µg/mL proteins. In some embodiments, the test reagent/composition in the container comprises about 55 µg/mL proteins.

In some embodiments, the cells are incubated in the upper chamber for about 6 to 72 hours. In some embodiments, the incubation period is from about 12 hours to 60 hours. In some embodiments, the incubation period is from about 18 hours to 48 hours. In some embodiments, the incubation period is any suitable value within these ranges. In some embodiments, the incubation period is about 6 hours. In some embodiments, the incubation period is about 18 hours. In some embodiments, the incubation period is about 24 hours. In some embodiments, the incubation period is about 30 hours. In some embodiments, the incubation period is about 36 hours. In some embodiments, the incubation period is about 42 hours. In some embodiments, the incubation period is about 48 hours.

In some embodiments, the total number of cells migrated through the membrane is measured by physical counting (image analysis software) with or without staining (colorimetric (e.g., Calcein AM) or fluorometric (e.g., crystal violet). In some embodiments, live-cell staining is used to quantify the migrated cells. In some embodiments, the total number of cells migrated through the membrane is measured by absorbance or fluorometric based methods to spectroscopically quantitate the cell mass. In some embodiments, the migrated cells are quantified by flow-cytometry.

In some embodiments, the FN composition of the present invention exhibits an ability to induce ocular wound healing in the transwell migration assay provided herein. In some embodiments, the FN composition of the present invention induces cell migration and/or proliferation in the transwell migration assay provided herein. In some embodiments, the FN composition of the present invention induces cell migration in the transwell migration assay provided herein. In some embodiments, the FN composition of the present invention induces cell proliferation in the transwell migration assay provided herein. In some embodiments, the FN composition of the present invention exhibits an ability to induce ocular wound healing in the transwell migration assay provided herein. In some embodiments, the FN composition of the present invention induces cell migration and/or proliferation in the transwell migration assay provided herein. In some embodiments, the FN composition of the present invention induces cell migration in the transwell migration assay provided herein. In some embodiments, the FN composition of the present invention induces cell proliferation in the transwell migration assay provided herein.

In some embodiments, the FN composition of the present invention increases cell migration and/or proliferation in the transwell assay by at least 1-fold, 2-fold, 3-fold, 4-fold, 5-fold, 6-fold, 7-fold, 8-fold, 9-fold, 10-fold or more. In some embodiments, the FN composition increases cell migration and/or proliferation in the transwell assay by at least 1-fold. In some embodiments, the FN composition increases cell migration and/or proliferation in the transwell assay by at least 2-fold. In some embodiments, the FN composition increases cell migration and/or proliferation in the transwell assay by at least 3-fold. In some embodiments, the FN composition increases cell migration and/or proliferation in the transwell assay by at least 4-fold. In some embodiments, the FN composition increases cell migration and/or proliferation in the transwell assay by at least 5-fold. In some embodiments, the FN composition increases cell migration and/or proliferation in the transwell assay by at least 6-fold. In some embodiments, the FN composition increases cell migration and/or proliferation in the transwell assay by at least 7-fold. In some embodiments, the FN composition increases cell migration and/or proliferation in the transwell assay by at least 8-fold. In some embodiments, the FN composition increases cell migration and/or proliferation in the transwell assay by at least 9-fold. In some embodiments, the FN composition increases cell migration and/or proliferation in the transwell assay by at least 10-fold. In some embodiments, the FN composition increases cell migration and/or proliferation in the transwell assay by at least 10%, 20%, 30%, 40%, 50%, 60%, 70%, 80%, 90%, 100%, or more. In some embodiments, the FN composition increases cell migration and/or proliferation in the transwell assay by at least 10%. In some embodiments, the FN composition increases cell migration and/or proliferation in the transwell assay by at least 20%. In some embodiments, the FN composition increases cell migration and/or proliferation in the transwell assay by at least 30%. In some embodiments, the FN composition increases cell migration and/or proliferation in the transwell assay by at least 40%. In some embodiments, the FN composition increases cell migration and/or proliferation in the transwell assay by at least 50%. In some embodiments, the FN composition increases cell migration and/or proliferation in the transwell assay by at least 60%. In some embodiments, the FN composition increases cell migration and/or proliferation in the transwell assay by at least 70%. In some embodiments, the FN composition increases cell migration and/or proliferation in the transwell assay by at least 80%. In some embodiments, the FN composition increases cell migration and/or proliferation in the transwell assay by at least 90%. In some embodiments, the FN composition increases cell migration and/or proliferation in the transwell assay by at least 100%.

In some embodiments, the FN composition increases cell migration and/or proliferation in the transwell assay by at least 1-fold, 2-fold, 3-fold, 4-fold, 5-fold, 6-fold, 7-fold, 8-fold, 9-fold, 10-fold or more. In some embodiments, the FN composition increases cell migration and/or proliferation in the transwell assay by at least 1-fold. In some embodiments, the FN composition increases cell migration and/or proliferation in the transwell assay by at least 2-fold. In some embodiments, the FN composition increases cell migration and/or proliferation in the transwell assay by at least 3-fold. In some embodiments, the FN composition increases cell migration and/or proliferation in the transwell assay by at least 4-fold. In some embodiments, the FN composition increases cell migration and/or proliferation in the transwell assay by at least 5-fold. In some embodiments, the FN composition increases cell migration and/or proliferation in the transwell assay by at least 6-fold. In some embodiments, the FN composition increases cell migration and/or proliferation in the transwell assay by at least 7-fold. In some embodiments, the FN composition increases cell migration and/or proliferation in the transwell assay by at least 8-fold. In some embodiments, the FN composition increases cell migration and/or proliferation in the transwell assay by at least 9-fold. In some embodiments, the FN composition increases cell migration and/or proliferation in the transwell assay by at least 10-fold. In some embodiments, the FN composition increases cell migration and/or proliferation in the transwell assay by at least 10%, 20%, 30%, 40%, 50%, 60%, 70%, 80%, 90%, 100%, or more. In some embodiments, the FN composition increases cell migration and/or proliferation in the transwell assay by at least 10%. In some embodiments, the FN composition increases cell migration and/or proliferation in the transwell assay by at least 20%. In some embodiments, the FN composition increases cell migration and/or proliferation in the transwell assay by at least 30%. In some embodiments, the FN composition increases cell migration and/or proliferation in the transwell assay by at least 40%. In some embodiments, the FN composition increases cell migration and/or proliferation in the transwell assay by at least 50%. In some embodiments, the FN composition increases cell migration and/or proliferation in the transwell assay by at least 60%. In some embodiments, the FN composition increases cell migration and/or proliferation in the transwell assay by at least 70%. In some embodiments, the FN composition increases cell migration and/or proliferation in the transwell assay by at least 80%. In some embodiments, the FN composition increases cell migration and/or proliferation in the transwell assay by at least 90%. In some embodiments, the FN composition increases cell migration and/or proliferation in the transwell assay by at least 100%.

In some embodiments, at least 30 µg/mL of the test reagent/composition is required to induce cell migration and/or proliferation in the transwell migration assay as provided herein. In some embodiments, at least 35 µg/mL of the test reagent/composition is required to induce cell migration and/or proliferation in the transwell migration assay as provided herein. In some embodiments, at least 40 µg/mL of the test reagent/composition is required to induce cell migration and/or proliferation in the transwell migration assay as provided herein. In some embodiments, at least 45 µg/mL of the test reagent/composition is required to induce cell migration and/or proliferation in the transwell migration assay as provided herein. In some embodiments, at least 50 µg/mL of the test reagent/composition is required to induce cell migration and/or proliferation in the transwell migration assay as provided herein.

In some embodiments, an endothelial cell tube formation assay can be performed on the FN composition. In some embodiments, an endothelial cell tube formation assays can be indicative that the FN composition is not pro-angiogenic. In some embodiments, an endothelial cell tube formation assay provides a measure of the angiogenic potential of the FN composition. In some embodiments, the FN composition exhibits anti-angiogenic properties. In some embodiments, the FN composition is anti-angiogenic properties. In some embodiments, an endothelial cell tube formation assay provides the ratio of anti-angiogenesis signals and pro-angiogenesis signals. In some embodiments, an endothelial cell tube formation assay a negative result will confirm the anti:pro ratio is high and will ensure the FN composition will not promote neovascularization. In some embodiments, an endothelial cell tube formation assay a negative result will confirm the anti: pro ratio is high and will ensure the FN composition will not promote CNV (choroidal neovascularization) or neovascularization in general. In some embodiments, an inhibition of TGFb (also referred to as TGFbeta or TGFβ) induced myofibroblast differentiation assay can be performed on the cellular FN composition. In some embodiments, an inhibition of TGFb induced myofibroblast differentiation assay can be performed on the cellular FN composition to show that the FN composition prevents scarring. In some embodiments, the FN composition prevents scarring. In some embodiments, the FN composition prevents scarring corneal opacity. In some embodiments, the cellular FN composition has low angiogenesis induction. In some embodiments, the FN composition has reduced angiogenic response. In some embodiments, the FN composition has reduced angiogenic capacity. In some embodiments, the FN composition impairs and/or reduces the normal formation of blood vessels in presence of media supportive of angiogenesis. In some embodiments, the FN composition has reduced angiogenic capacity when the FN composition is compared to untreated control. In some embodiments, the FN composition has reduced angiogenic capacity as compared to a sample treated to serum containing media. In some embodiments, the FN composition attenuates an angiogenic response. In some embodiments, the FN composition reduces the angiogenic response induce by serum free media. In some embodiments, a reduction in angiogenic response is induced by the FN composition when secretome plus serum containing media (reduced or no angiogenic response) is compared to serum containing media (angiogenic response). In some embodiments, an angiogenic response is indicated by tube formation in a cell-based assay. In some embodiments, an angiogenic response is indicated by tube formation in an endothelial cell tube formation assay.

Differentiation/Scarring:

In some embodiments, the FN composition can be evaluated for the ability to prevent differentiation and prevent scarring. In some embodiments, the FN composition prevents and/or impairs scarring. In some embodiments, the FN composition prevents scarring. In some embodiments, the FN composition reduces scarring as compared to other standard treatments. In some embodiments, the FN composition prevents and/or impairs differentiation. In some embodiments, the FN composition prevents and/or impairs myofibroblast differentiation. In some embodiments, the FN composition reduces the loss of corneal transparency. In some embodiments, the FN composition reduces the loss of corneal transparency by preventing and/or impairing myofibroblast differentiation.

In some embodiments, the FN composition can be evaluated for the ability of the FN composition to modulate factors involved in differentiation. In some embodiments, the FN composition can be evaluated the ability of the FN composition to modulate factors involved in differentiation, including but not limited to TGFB2, Collagen I, Collagen III (normally upregulated during differentiation), TFGB3, MMP-2, and MMP-9 (normally downregulated during differentiation. In some embodiments, the cellular FN composition modulates factors selected from the group consisting of TGFB2, Collagen I, Collagen III (normally upregulated during differentiation), TFGB3, MMP-2, and MMP-9 (normally downregulated during differentiation. In some embodiments, the FN composition induces a decrease in factors upregulated during normal differentiation. In some embodiments, the FN composition induces an increase in factors downregulated during normal differentiation. In some embodiments, the cellular FN composition induces a decrease in expression of factors such as SMA. In some embodiments, the FN composition induces a decrease in expression of factors such as SMA which is indicative of FN composition potency.

Neovascularization:

In some embodiments, the FN composition can be evaluated for the ability to prevent neovascularization. In some embodiments, the FN composition prevents, impairs, inhibits, and/or reduces neovascularization. In some embodiments, the FN composition inhibits or does not promote neovascularization. In some embodiments, the FN composition can be evaluated for the ability to prevent angiogenesis. In some embodiments, the FN composition prevents, impairs, inhibits, and/or reduces angiogenesis. In some embodiments, the FN composition inhibits angiogenesis.

In some embodiments, the FN composition can be further evaluated using depletion assays. In some embodiments, the FN composition can be depleted of specified factors. In some embodiments, the FN composition can be depleted of specified factors, including for example, but not limited to TIMP1 and/or Serpin E1. In some embodiments, the FN composition can be depleted of TIMP1 and/or Serpin E1. In some embodiments, the FN composition can be depleted of TIMP1. In some embodiments, the FN composition can be depleted of Serpin E1.

Inflammation:

In some embodiments, the FN composition can be evaluated for the ability to prevent, impair, inhibit, and/or reduce inflammation. In some embodiments, the FN composition prevents, impairs, inhibits, and/or reduces inflammation. In some embodiments, the FN composition inhibits inflammation. In some embodiments, the FN composition is characterized in vitro and/or in vivo to determine the ability to prevent, impair, inhibit, and/or reduce inflammation. In some embodiments, the FN composition prevents, impairs, inhibits, and/or reduces inflammation in vitro and/or in vivo. In some embodiments, the FN composition prevents, impairs, inhibits, and/or reduces inflammation in vitro. In some embodiments, the FN composition prevents, impairs, inhibits, and/or reduces inflammation or in vivo. In some embodiments, a tissue model can be employed to characterizing preventing, impairing, inhibiting, and/or reducing inflammation in vitro. In some embodiments, a 3D tissue model can be employed to characterizing preventing, impairing, inhibiting, and/or reducing inflammation in vitro. In some embodiments, a nitrogen mustard (NM) gas burn model can be used to evaluate preventing, impairing, inhibiting, and/or reducing inflammation in vitro. In some embodiments, a nitrogen mustard (NM) gas burn model can be used to evaluate preventing, impairing, inhibiting, and/or reducing inflammation in vitro and as a surrogate for in vivo conditions. In some embodiments, the cytokine profile in response to treatment with and/or administration of the FN composition can be determined. In some embodiments, the levels of specific cytokines can be determined. In some embodiments, the level of IL-8 can be determined. In some embodiments, the level of IL-8 expression can be reduced in tissues treated with the FN composition. In some embodiments, the level of IL-8 expression is reduced in tissues treated with the FN composition and this is indicative of preventing, impairing, inhibiting, and/or reducing inflammation.

E. Methods of Treatment

The present disclosure also provides methods of treatment using the FN composition, such as the cellular FN composition, optionally comprising one or more growth factors selected from the group consisting of FGFs (such as FGF-2), PDGF, HGF, VEGF, TGFβ1, TGFβ2, IGF-1, IGF-2, NGF, neurotrophins, and EGF. In particular, the FN composition finds use in the treatment of ocular conditions. In particular, the FN composition finds use in the treatment of ocular conditions, including but not limited to ocular diseases. In some embodiments, the ocular disease is associated with the ocular surface. In some embodiments, the ocular disease is associated with damaged ocular tissue and/or damaged ocular tissue indications. In some embodiments, the FN composition finds use in the treatment of ocular conditions, including accelerating wound healing. In some embodiments, the FN composition finds use in the treatment of ocular conditions, including reducing scarring. In some embodiments, the FN composition finds use in the treatment of ocular conditions, including reducing inflammation. In some embodiments, the FN composition finds use in the treatment of ocular conditions, including reducing inflammation and thus promoting growth. In some embodiments, the FN composition finds use in treating ocular conditions such as reducing inflammation at the ocular surface. In some embodiments, the FN composition finds use in the treatment of ocular conditions, including reducing neovascularization. In some embodiments, the FN composition finds use in the treatment of ocular conditions, including reducing neovascularization in the cornea. In some embodiments, the FN composition finds use in the treatment of ocular conditions, including dry eye treatment (including, for example, treatment of severe dry eye, including where the epithelial cells are damaged). In some embodiments, the FN composition finds use in the treatment of ocular conditions, such as restoring the integrity to damaged ocular tissue. In some embodiments, the FN composition finds use in the treatment of ocular conditions, such as accelerating the healing of damaged ocular tissue. In some embodiments, the FN composition finds use in the treatment of ocular conditions, such as regenerating damaged ocular nerve tissue. In some embodiments, the FN composition finds use in the treatment of ocular conditions, such as a retina condition. In some embodiments, the FN composition finds use in the treatment of ocular conditions, such as regenerating damaged ocular nerve tissue associated with PCED. In some embodiments, the FN composition finds use in the treatment of ocular conditions, such as PCED. In some embodiments, the FN composition finds use in the treatment of ocular conditions, such as inflammatory damage to the eye surface. In some embodiments, the FN composition finds use in the treatment of ocular conditions, such as for example GvHD and/or Sjogrens syndrome.

In some embodiments, the ocular condition is selected from the group consisting of retina condition, Chronic Graft v. Host Disease (GvHD), Stevens-Johnson Syndrome, Ocular Mucous Membrane Pemphigoid, Persistent Corneal Epithelial Defect (PCED), dry eye, ocular nerve tissue damage, and concussive injury to the eye (such as concussive injury, ocular contusion, or chemical burn).

In some embodiments, the FN composition finds use in accelerating wound healing. In some embodiments, the FN composition finds use in reducing scarring. In some embodiments, the FN composition finds use in reducing inflammation. In some embodiments, the FN composition finds use in reducing inflammation and thus promoting growth. In some embodiments, the FN composition finds use in reducing inflammation at the ocular surface. In some embodiments, the FN composition finds use in reducing neovascularization. In some embodiments, the FN composition finds use in reducing neovascularization in the cornea. In some embodiments, the FN composition finds use in the protection and repair of retinal epithelial cells and retinal ganglion cells. In some embodiments, the FN composition finds use in induction of trabecular meshwork regeneration and reduction of intraocular pressure.

In some embodiments, the FN composition is administered for the treatment of an ocular disease. In some embodiments, treatment comprises administering to a patient in need thereof therapeutically effective amount of a FN composition as described herein to a patient in need thereof. In some embodiments, the FN composition is administered to a patient in need thereof in order to promote or induce ocular wound healing. In some embodiments, the FN composition is administered to a patient in need thereof in order to reduce and/or inhibit neovascularization, reduce and/or inhibit scarring, promote and/or preserve vision, and/or increasing wound closure rate (e.g., decreasing wound closure time). In some embodiments, the FN composition is administered to a patient in need thereof in order to prevent, reduce, and/or inhibit neovascularization. In some embodiments, the FN composition is administered to a patient in need thereof in order to prevent, reduce, and/or inhibit reducing scarring. In some embodiments, the FN composition is administered to a patient in need thereof in order to promote and/or preserve vision. In some embodiments, the FN composition is administered to promote and/or induce closing wound faster wound closure (e.g., reduce the amount of time required for wound closure). In some embodiments, the FN composition prevents, reduces, and/or inhibits or does not promote neovascularization and reducing scarring in order to promote vision preservation. In some embodiments, the FN composition is administered to a patient in need thereof in order to prevent, reduce, and/or inhibit neovascularization and reducing scarring in order to promote vision preservation. In some embodiments, the FN composition prevents, reduces, and/or inhibits inflammation. In some embodiments, the FN composition is administered to a patient in need thereof in order to prevent, reduce, and/or inhibit inflammation.

In some embodiments, the FN composition is administered for the treatment of a visual dysfunction following traumatic injury to ocular structures. In some embodiments, treatment comprises administering to a patient in need thereof a therapeutically effective amount of a FN composition as described herein In some embodiments, the FN composition is administered for the treatment of a traumatic injury of the optic nerve degeneration following concussive injury. In some embodiments, the concussive injury to the eye is selected from the group consisting of ocular contusion and blunt injury to the eye. In some embodiments, the FN composition is administered for the treatment of a traumatic injury of the optic nerve. In some embodiments, treatment comprises administering to a patient in need thereof a therapeutically effective amount of a FN composition as described herein.

In some embodiments, the FN composition is administered for ameliorating optic nerve degeneration following concussive injury to the eye. In some embodiments the method for ameliorating optic nerve degeneration comprises administering to the patient a therapeutically effective amount of a FN composition as described herein. In some embodiments, the concussive injury to the eye is selected from the group consisting of ocular contusion and blunt injury to the eye. In some embodiments, the concussive injury to the eye an ocular contusion. In some embodiments, the concussive injury to the eye a blunt injury to the eye.

Efficacy readouts can include a reduced in symptoms and/or decreased disease state, including for example, increased quality of life. In some embodiments, reduced in symptoms and/or decreased disease state by 10%, 20%, 30%, 40%, 50%, 60%, 70%, 80%, 90%, 95%, or 100% is indicative of therapeutic efficacy. In some embodiments, reduction in inflammation by 10%, 20%, 30%, 40%, 50%, 60%, 70%, 80%, 90%, 95%, or 100% is indicative of therapeutic efficacy. In some embodiments, a reduction in scarring by 10%, 20%, 30%, 40%, 50%, 60%, 70%, 80%, 90%, 95%, or 100% is indicative of therapeutic efficacy. In some embodiments, a reduction in neovascularization by 10%, 20%, 30%, 40%, 50%, 60%, 70%, 80%, 90%, 95%, or 100% is indicative of therapeutic efficacy.

In some embodiments, the disease or conditions an ocular disease or ocular condition. In some embodiments, the disease or condition is a visual dysfunction following traumatic injury to ocular structures. In some embodiments, the disease or condition is a concussive (e.g., blunt or non-blunt) injury to the eye. In some embodiments, the disease or condition is a burn, including a chemical burn to the eye.

In some embodiments, the FN composition is administered to a particular targeted area. In some embodiments, the particular targeted area is the eye. In some embodiments, the FN composition is administered to a particular targeted area and is formulated so as not to spread to other surrounding areas.

In some embodiments, the FN composition is administered to a particular targeted area and is formulated so as not to spread to other surrounding areas.

In some embodiments, the FN composition is administered to a particular targeted area and is formulated to stay in the targeted area for at least 1 minute, at least about 2 minutes, 3 at least about minutes, at least about 4 minutes, at least about 5 minutes, at least about 10 minutes, at least about 15 minutes, at least about 20 minutes, at least about 30 minutes, at least about 40 minutes, at least about 50 minutes, at least about 60 minutes, at least about 70 minutes, at least about 80 minutes, at least about 90 minutes, or at least about 2 hours.

In some embodiments, the FN composition is administered to an affected area immediately after the wound or injury. In some embodiments, the FN composition is administered to an affected area within 15 seconds, 30 seconds, 1 minutes, 2 minutes, 3 minutes, 4 minutes, 5 minutes, 10 minutes, 15 minutes, 20 minutes, 30 minutes, 40 minutes, 50 minutes, 60 minutes, 70 minutes, 80 minutes, 90 minutes, 2 hours, 4 hours, 8 hours, 12 hours, 24 hours, 36 hours, 48 hours, or 96 hours.

In some embodiments, the FN composition is administered topically. In some embodiments, the cellular FN composition is administered by subconjunctival injection. In some embodiments, the FN compositions exhibit ultrapotency when administered to a subject in need thereof. In some embodiments, the FN composition is administered topically once, two, three, four, five, and/or up to six times daily. In some embodiments, the FN compositions allow for therapeutic efficacy with one drop or one administration per day. In some embodiments, one drop is administered 1, 2, 3, 4, 5, or 6 times per day. In some embodiments, one drop is administered at 1 hour, 2 hour, 3 hour, or 4 hour intervals. In some embodiments, one drop is administered at least once per day for 1 week, 2 weeks, 3 weeks, 4 weeks, 5 weeks, 6 weeks, 7 weeks, 8 weeks, 9 weeks, or 10 weeks. In some embodiments, one drop is administered at least twice per day for 1 week, 2 weeks, 3 weeks, 4 weeks, 5 weeks, 6 weeks, 7 weeks, 8 weeks, 9 weeks, or 10 weeks. In some embodiments, one drop is administered at least 3 times per day for 1 week, 2 weeks, 3 weeks, 4 weeks, 5 weeks, 6 weeks, 7 weeks, 8 weeks, 9 weeks, or 10 weeks. In some embodiments, one drop is administered at least 4 times per day for 1 week, 2 weeks, 3 weeks, 4 weeks, 5 weeks, 6 weeks, 7 weeks, 8 weeks, 9 weeks, or 10 weeks. In some embodiments, one drop is administered at least 5 times per day for 1 week, 2 weeks, 3 weeks, 4 weeks, 5 weeks, 6 weeks, 7 weeks, 8 weeks, 9 weeks, or 10 weeks. In some embodiments, one drop is administered at least 6 times per day for 1 week, 2 weeks, 3 weeks, 4 weeks, 5 weeks, 6 weeks, 7 weeks, 8 weeks, 9 weeks, or 10 weeks.

In some embodiments, the FN composition for use in the methods of treatment further comprises low levels for VEGF. In some embodiments, the FN composition for use in the methods of treatment further comprises 1 pg/mL-400 pg/mL of VEGF.

In some embodiments, the FN composition for use in the methods of treatment has a pH of about 4.7 to about 7.5.

In some embodiments, the FN composition for use in the methods of treatment is formulated in a buffer system selected from the group consisting of di/mono sodium phosphate, sodium citrate/citric acid, boric acid/sodium citrate, boric acid/sodium tetraborate, and citric acid/disodium phosphate.

In some embodiments, the FN composition for use in the methods of treatment further comprises a tonicity modifying agent. In some embodiments, the tonicity modifying agent is selected from the group consisting of NaCl, KCl, mannitol, dextrose, sucrose, sorbitol, and glycerin.

In some embodiments, the FN composition for use in the methods of treatment further comprises mono/di-sodium phosphate, mannitol, and trehalose, and wherein the composition has a pH of about pH 7.4.

In some embodiments, the FN composition for use in the methods of treatment further comprises divalent cations. In some embodiments, the divalent cations are selected from the group consisting of Mg2+, Ca2+, and Zn2+.

In some embodiments, the FN composition for use in the methods of treatment further comprises di-sodium phosphate/citric acid, mannitol, and trehalose, and wherein the composition has a pH of about pH 6.4.

In some embodiments, the FN composition for use in the methods of treatment further comprises an adhesive agent.

In some embodiments, the FN composition for use in the methods of treatment does not comprise one or more components selected from the group consisting of: xenobiotic components; Phenol red; peptides and biomolecules <3 kDa; antibiotics; protein aggregates >200 nm; cells; non-exosome/non-Extracellular Vesicles cell debris; hormones; and L-glutamine.

In some embodiments, the FN composition for use in the methods of treatment comprise an anti-angiogenic or an anti-scarring factor.

F. KIT

A kit can include a FN composition in a container or the conditioned media for use in preparing a FN composition, also in a container, as disclosed herein, and instructions for use. Additionally, a kit can include components for mixing to prepare a solution for use in an ocular treatment, and instructions for mixing and use.

The container can include at least one vial, well, test tube, flask, bottle, syringe, or other container means, into which a FN composition in a container or the conditioned media for use in preparing a FN composition, and in some instances, suitably aliquoted. Where an additional component is provided, the kit can contain additional containers into which this component may be placed. Such containers may include injection or blow-molded plastic containers into which the desired vials are retained. Containers and/or kits can include labeling with instructions for use and/or warnings.

The present disclosure is further illustrated by the following examples, which should not be construed as further limiting. The contents of all figures and all references, Genbank sequences, patents and published patent applications cited throughout this application are expressly incorporated herein by reference.

The present invention can provide kits comprising a panel of tests and/or assays for characterizing a MSC secretome, wherein the panel comprises at least two characterization assays, wherein characterization assays are selected from the group consisting of physical component characterizations, oxidative stress assays, safety analyses, stability assays, proliferation assays, migration assays, neovascularization assays, differentiation/scarring assays, inflammation assays, and/or an epithelial barrier integrity assays. In some embodiments, the panel of tests and/or assays identifies a MSC secretome as described herein.

The present invention can provide kits comprising a panel of tests and/or assays for determining consistency between FN lots, wherein the panel comprises one or more characterization assays, wherein characterization assays are selected from the group consisting of physical component characterizations, oxidative stress assays, safety analyses, stability assays, proliferation assays, migration assays, neovascularization assays, differentiation/scarring assays, inflammation assays, and/or an epithelial barrier integrity assays. In some embodiments, the panel of tests and/or assays identifies a cellular FN composition as described herein.

EXAMPLES

Example 1: Fibronectin Characterization

FN was Identified in MSC Secretome MSC Secretome Initially through Mass Spec and Subsequently Quantified via ELISA FN was detected in conditioned media (i.e., the media directly harvested off cells) at concentration of ~0.5-50 ng/mL.

Results of Cell-Based In Vitro Assays Showed:

Depletion of FN significantly impaired wound closure (Scratch Wound Assay)

Addition of MSC secretome promoted adherence and spreading of HCECs; depletion of FN impaired adherence and spreading of HCECs; addition of exogenous FN promoted adherence and spreading of HCECs Addition of exogenous fibronectin promotes HCEC transwell migration; depletion of FN impairs HCEC transwell migration
Fibronectin Stimulates Human Corneal Epithelial Cell Migration.

Figure 2:
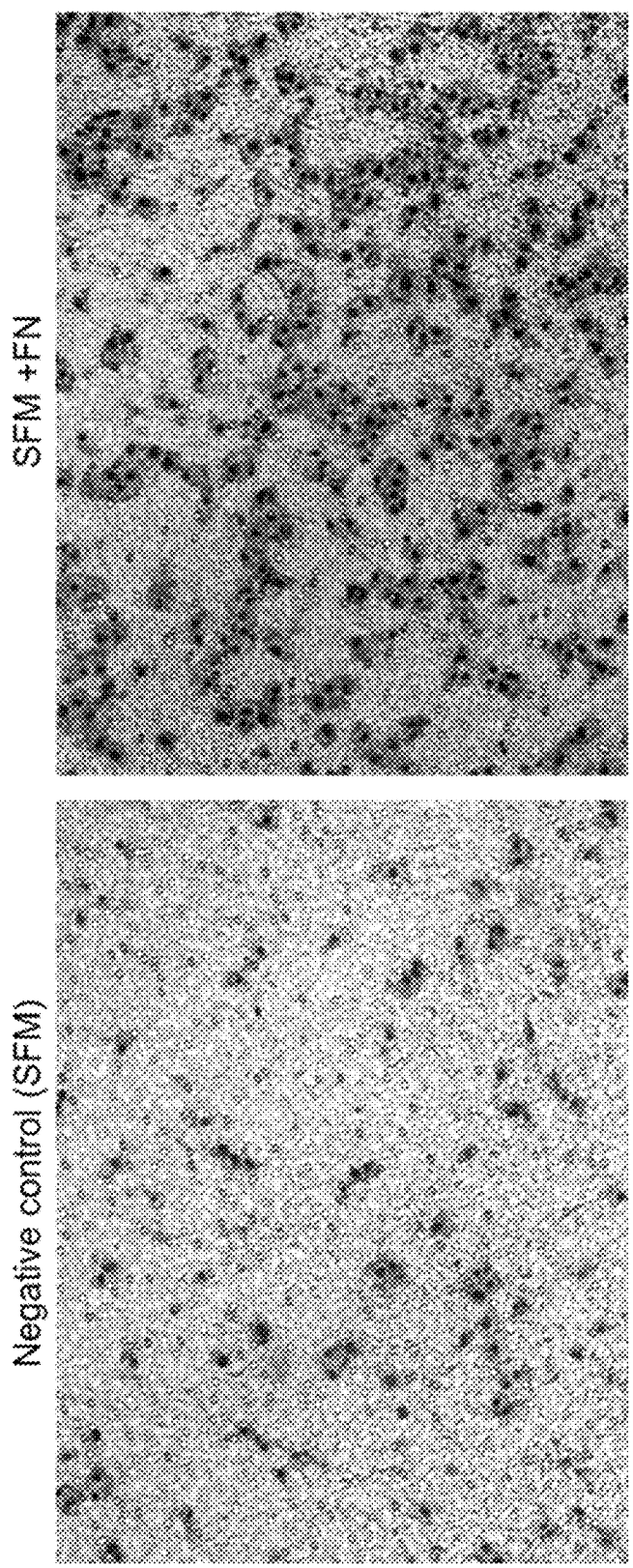
FIG. 2. Fibronectin stimulates human corneal epithelial cell migration.

Addition of exogenous recombinant human Fibronectin (1 ug/mL) stimulates significant migration of cells through the transwell membrane after 36 hr relative to negative control (serum free media). Depicted is the bottom side of a transwell migration insert stained with Gentian Violet (FIG. 2).
Depletion of Fibronectin Impairs the Migration of Human Corneal Epithelial Cells.

Figure 3:
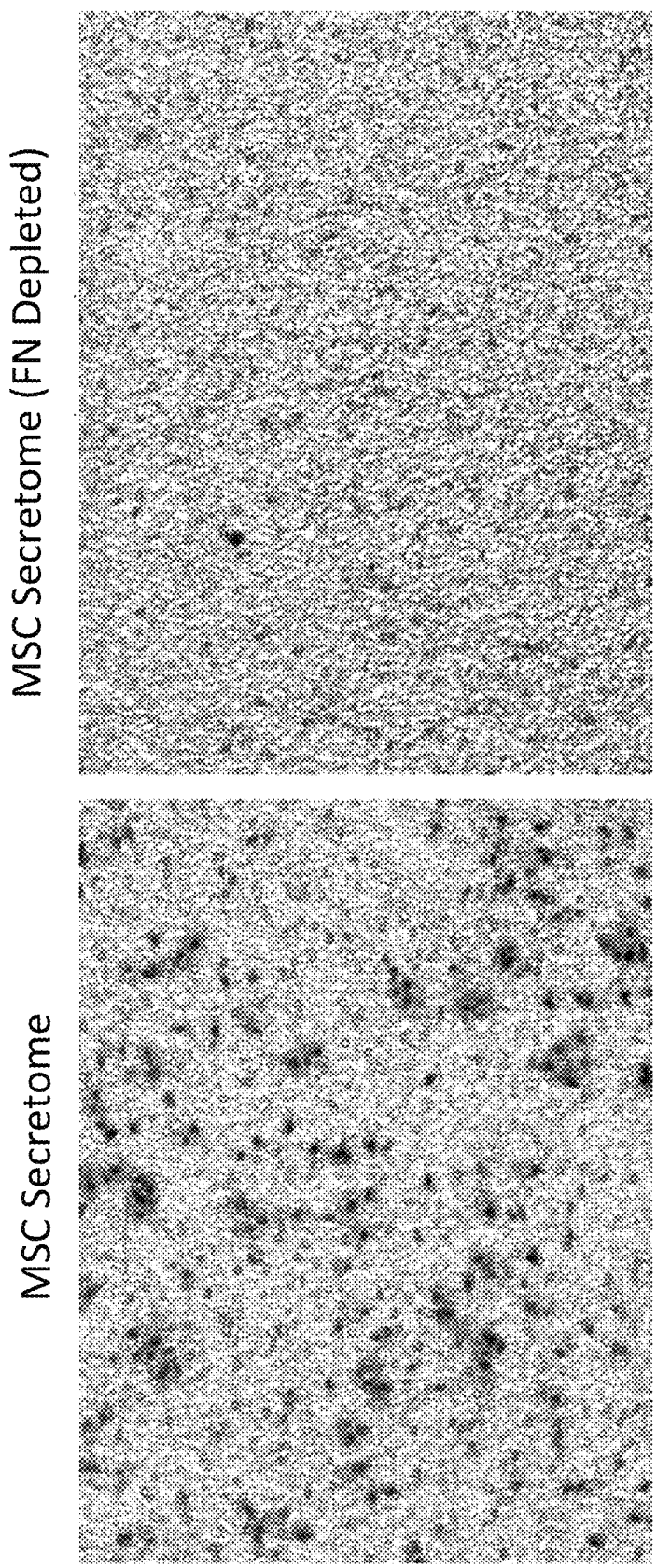
FIG. 3. Depletion of Fibronectin impairs the migration of human corneal epithelial cells.

MSC secretome Immuno-depleted for Fibronectin demonstrates impaired migration relative to MSC secretome alone in a transwell migration assay. Depicted is the bottom side of a transwell migration insert stained with Gentian Violet (FIG. 3).
Depletion of Fibronectin Impairs Human Corneal Epithelial Cell In Vitro Wound Closure.

MSC secretome Immuno-depleted for Fibronectin demonstrates impaired migration of cells into the wound gap relative to MSC secretome alone in a transwell migration assay. After 24 hours, MSC secretome treated cells demonstrated 30±1.2% closure compared to 16±1.9% closure in FN-depleted MSC secretome treated wounds (FIG. 4).

Example 2: Fibronectin is Bound to Growth Factors

Fibronectin sas Immunodepleted from MSC Secretome using Anti-Fibronectin Capture Antibodies and Pulled Down Using Protein G Conjugated Magnetic Beads The in-solution fraction as well as the bead fraction were assayed for HGF via ELISA. The beads were washed three times with PBS and resuspended in 100 uL PBS, followed by heating for 10 minutes at 80° C. The sample was then diluted as measured by ELISA using recombinant HGF to generate a standard curve See FIG. 5 for HGF assay results in pg/mL.

Example 3: MSC Secretome Contains Cellular Fibronectin

Figure 6:
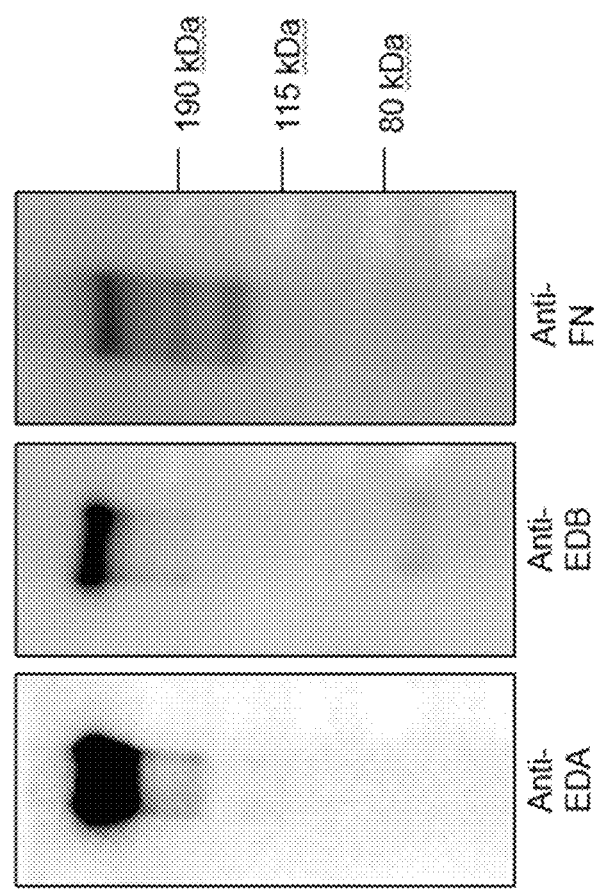
FIG. 6. Characterization of fibronectin in secretome. The secretome isolated from MSCs was evaluated by immunoblotting using antibodies specific for the EDA sequence, EDB+ fibronectin, and a general Fibronectin (FN). Both anti-EDA and anti-EDB antibodies cross-reacted with fibronectin indicating that the species present in the secretome is cellular fibronectin.
Figure 7:
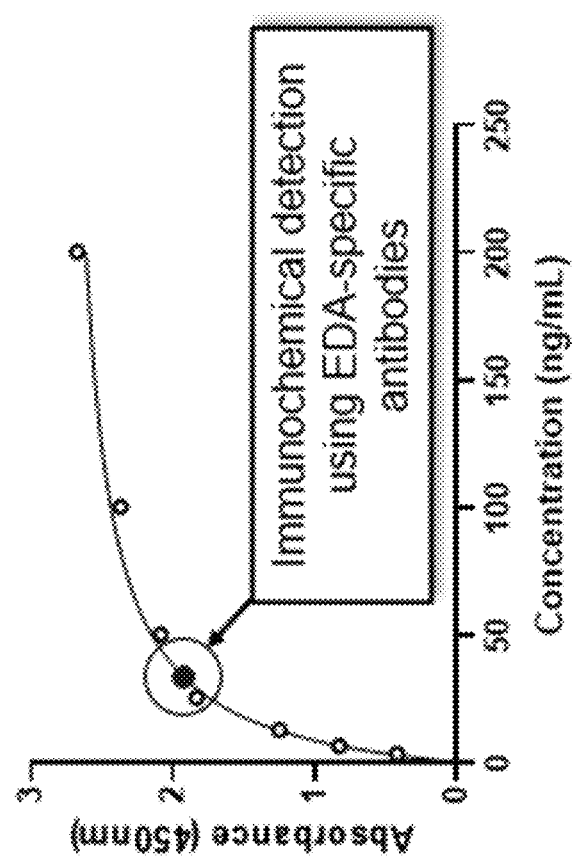
FIG. 7. Detection of Cellular EDA+ Fibronectin using sandwich ELISA. An ELISA standard curve (open circles) for EDA+ Fibronectin was established using recombinant cellular fibronectin and a capture antibody specific for the EDA sequence. The recombinant fibronectin used to generate the standard curve contained the EDA sequence used as immunogen to generate the anti-EDA antibody. MSC secretome was assayed in the EDA sandwich ELISA and cellular Fibronectin was readily detected (blue dot).

MSC secretome was analyzed using immunological assays. The results demonstrate that the MSC secretome contained cellular fibronectin, as evidenced by detection of EDA+ and EDB+ fibronectin splicing variants.
Characterization of Fibronectin in Secretome The secretome isolated from MSCs was evaluated by immunoblotting using antibodies specific for the EDA sequence, EDB+ fibronectin, and a general Fibronectin (FN). Both anti-EDA and anti-EDB antibodies cross-reacted with fibronectin indicating that the species present in the secretome is cellular fibronectin (FIG. 6).
Detection of Cellular EDA+ Fibronectin using Sandwich ELISA An ELISA standard curve (open circles) for EDA+ Fibronectin was established using recombinant cellular fibronectin and a capture antibody specific for the EDA sequence. The recombinant fibronectin used to generate the standard curve contained the EDA sequence used as immunogen to generate the anti-EDA antibody. MSC secretome was assayed in the EDA sandwich ELISA and cellular Fibronectin was readily detected (blue dot) (FIG. 7).

What is claimed is:

1. A method of making a composition comprising mesenchymal stem cell (MSC)-derived fibronectin (FN), comprising:
   (a) culturing mesenchymal stem cells (MSCs) in a cell culture medium, thereby generating conditioned medium that comprises factors comprising MSC-derived FN secreted by the MSCs;
   (b) harvesting the conditioned medium thereby producing harvested conditioned medium; and
   (c) filtering harvested conditioned medium to produce processed conditioned medium;
   wherein the MSCs are bone marrow-derived.

2. The method according to claim 1, wherein step (a) comprises:
   (i) culturing the MSCs in a first culture medium;
   (ii) removing the first culture medium from step (i) from the MSCs;
   (iii) washing the MSCs in step (ii); and
   (iv) adding a second culture medium and culturing for about 1-5 days.

3. The method according to claim 2, wherein the first and/or second culture medium is selected from the group consisting of: hMSC Media Booster XFM, hMSC High Performance Basal Media, Minimum Essential Medium Eagle (MEME), ADC-1, LPM (Bovine Serum Albumin-free), F10 (HAM), F12 (HAM), DCCM1, DCCM2, RPMI 1640, BGJ Medium (with and without Fitton-Jackson Modification), StemPro, MSCGro, MesenCult, NutriStem, Basal Medium Eagle (BME—with the addition of Earle's salt base), Dulbecco's Modified Eagle Medium (DMEM—with or without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Alpha (MEM-alpha), Minimum Essential Medium Eagle (MEM-E—with Earle's salt base), Minimum Essential Medium Eagle (MEM-H—with Hank's salt base), Minimum Essential Medium Eagle (MEM-NAA with non-essential amino acids), medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, and MDBC 153.

4. The method according to claim 2, wherein the first and/or second culture medium is MSC Media and/or MSC-XF.

5. The method according to claim 2, wherein the first and/or second culture medium is a serum-free medium.

6. The method according to claim 2, wherein the first and/or second culture medium is supplemented with serum.

7. The method according to claim 2, wherein the first and/or second culture medium is supplemented with human platelet lysate.

8. The method according to claim 1, wherein the MSCs of step (a) are cultured in a first medium that is a growth factor-containing medium prior to being cultured in second medium that is growth factor-free at the time of being added to the MSCs.

9. The method according to claim 1, wherein the culturing step (a) comprises growing the MSCs under a low oxygen partial pressure environment to facilitate cell growth and/or promote cell health.

10. The method according to claim 9, wherein in the culturing step (a) the oxygen is at 5%, 10%, 15%, 20%, or 25%.

11. The method according to claim 1, wherein the filtering step (c) comprises using a 0.45 μm filter, a 0.22 μm filter, 0.8 μm filter, and 0.65 μm filter, a low protein binding polyvinylidene difluoride (PVDF) membrane, and/or a PES (polyethersulfone) membrane.

12. The method according to claim 1, wherein the filtering step (c) comprises using cross-flow filtration.

13. The method according to claim 1, wherein step (c) comprises:
(1) filtering the harvested conditioned medium from step (b) to remove cell particulate;
(2) concentrating the filtered conditioned medium; and
(3) buffer exchanging with a formulation buffer.

14. The method according to claim 13, wherein the concentrating step (2) comprises using hollow fiber filters, tangential flow filtration systems, or centrifugation based size exclusion techniques.

15. The method according to claim 13, wherein the concentrating step (2) comprises using a centrifugation based size exclusion technique, wherein centrifugation based size exclusion technique employs a 3 kDa MW cutoff, at least a 4 kDa MW cutoff, at least a 5 kDa MW cutoff, at least a 6 kDa MW cutoff, at least a 7 kDa MW cutoff, at least a 8 kDa MW cutoff, at least a 9 kDa MW cutoff, at least a 10 kDa MW cutoff, at least a 11 kDa MW cutoff, at least a 12 kDa MW cutoff, at least a 13 kDa MW cutoff, at least a 14 kDa MW cutoff, at least a 15 kDa MW cutoff, at least a 16 kDa MW cutoff, at least a 17 kDa MW cutoff, at least a 18 kDa MW cutoff, at least a 19 kDa MW cutoff, at least a 20 kDa MW cutoff, at least a 21 kDa MW cutoff, at least a 22 kDa MW cutoff, at least a 23 kDa MW cutoff, at least a 24 kDa MW cutoff, at least a 25 kDa MW cutoff, at least a 26 kDa MW cutoff, at least a 27 kDa MW cutoff, at least a 28 kDa MW cutoff, at least a 29 kDa MW cutoff, and/or at least a 30 kDa MW cutoff.

16. The method according to claim 13, wherein in the concentrating step (2) the filtered conditioned medium is concentrated about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, or about 100-fold.

17. The method according to claim 13, wherein the buffer exchanging step (3) comprises buffer exchanging with a buffer system selected from the group consisting of di/mono sodium phosphate, sodium citrate/citric acid, boric acid/sodium citrate, boric acid/sodium tetraborate, and citric acid/disodium phosphate.

18. The method according to claim 13, wherein in the buffer exchanging step (3) the conditioned medium is diluted less than 1%, less than 5%, less than 10%, less than 15%, less than 20%, or less than 25%.

19. The method according to claim 13, wherein in the buffer exchanging step (3) the conditioned medium is buffer exchanged after the concentration step such that less than about 25%, less than about 20%, less than about 15%, less than about 10%, less than about 5%, less than about 4%, less than about 3%, less than about 2%, or less than about 1% or about 0% of the culture medium components remain.

20. The method according to claim 1, further comprising characterizing the composition comprising MSC-FN using one or more assays selected from the group consisting of: a transwell migration assay, a human corneal epithelial cell proliferation assays, an endothelial cell tube formation assay, an oxidative stress prevention assays, a blood compatibility assay for hemolysis and hemagglutination, a depletion assay, a protein array assay, an enzyme-linked immunosorbent assay (ELISA), a mass spectrometry assay, and an immunoblotting assay.

* * * * *